(12) United States Patent
Ino et al.

(10) Patent No.: US 6,635,662 B2
(45) Date of Patent: Oct. 21, 2003

(54) RADICICOL DERIVATIVES

(75) Inventors: Yoji Ino, Shizuoka (JP); Nobuyoshi Amishiro, Shizuoka (JP); Mayumi Miyata, Shizuoka (JP); Chikara Murakata, Shizuoka (JP); Harumi Ogawa, Tokyo (JP); Tadakazu Akiyama, Shizuoka (JP); Shiro Akinaga, Shizuoka (JP); Shiro Soga, Shizuoka (JP); Yukimasa Shiotsu, Shizuoka (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 118 days.

(21) Appl. No.: 09/791,602

(22) Filed: Feb. 26, 2001

(65) Prior Publication Data

US 2001/0027208 A1 Oct. 4, 2001

Related U.S. Application Data

(62) Division of application No. 09/513,472, filed on Feb. 25, 2000, now Pat. No. 6,239,168, which is a division of application No. 09/091,752, filed on Jun. 24, 1998, now Pat. No. 6,316,491.

(30) Foreign Application Priority Data

Oct. 25, 1996 (JP) .............................................. 8-284439
Jan. 13, 1997 (JP) .............................................. 9-003578

(51) Int. Cl.$^7$ ...................... A61K 31/44; A61K 31/335; C07D 405/12; C07D 313/08
(52) U.S. Cl. .................. 514/337; 514/63; 514/450; 546/281.7; 549/214; 549/270
(58) Field of Search ...................... 546/281.7; 514/337, 514/63, 321, 450; 549/270, 214

(56) References Cited

U.S. PATENT DOCUMENTS

| | | | |
|---|---|---|---|
| 5,597,846 A | 1/1997 | Sugimura et al. ........... | 514/450 |
| 5,650,430 A | 7/1997 | Sugimura et al. ........... | 514/450 |
| 5,731,343 A | 3/1998 | Feng et al. .................. | 514/450 |
| 5,977,165 A | * 11/1999 | Agatsuma et al. .......... | 514/450 |

FOREIGN PATENT DOCUMENTS

| | | |
|---|---|---|
| EP | 0 823 429 | 2/1998 |
| JP | 4226991 | 8/1992 |
| JP | 6-279279 | 10/1994 |
| JP | 6-298764 | 10/1994 |
| JP | 8-40893 | 2/1996 |
| JP | 9-202781 | 8/1997 |
| WO | 96/33 989 | 10/1996 |

OTHER PUBLICATIONS

The Journal of Biological Chemistry, vol. 270, No. 41, Oct. 13, 1995, p. 24585–24588.
Proc. Natl. Acad. Sci. USA, vol. 91, Aug. 1994, pp. 8324–8328.
Cancer Research 54, May 15, 1994, pp. 2724–2730.
Cancer Research 52, Apr. 1, 1992, pp. 1721–1728.
Journal of Antibiotics, vol. XXIII, No. 9, Sep. 1970, pp. 442–447.
Nature, vol. 171, Feb. 21, 1953, p. 344.
Neoplasma 24, 1, 1977, pp. 21–27.
Oncogene (1995) 11, pp. 161–173.
The Journal of Biological Chemistry, vol. 270, No. 1041 (1995), p. 5418–5426.

* cited by examiner

Primary Examiner—Joseph K. McKane
Assistant Examiner—Ebenezer Sackey
(74) Attorney, Agent, or Firm—Fitzpatrick, Cella, Harper & Scinto

(57) ABSTRACT

Radicicol derivatives represented by the following formula (I) having tyrosine kinase inhibition activity or pharmacologically acceptable salts thereof:

(I)

wherein $R^1$ and $R^2$ are the same or different, and each represents hydrogen, alkanoyl, alkenoyl, tert-butyldiphenylsilyl or tert-butyldimethylsilyl; $R^3$ represents Y—$R^5$ {wherein Y represents substituted or unsubstituted alkylene; and $R^5$ represents $CONR^6R^7$ (wherein $R^6$ represents hydrogen, hydroxyl, substituted or unsubstituted lower alkyl, substituted or unsubstituted higher alkyl, and the like; $R^7$ represents hydroxyl, substituted lower alkyl, and the like), $CO_2R^{12}$ (wherein $R^{12}$ represents substituted lower alkyl, substituted or unsubstituted higher alkyl, and the like), and the like} and the like; X represents halogen or is combined together with $R^4$ to represent a single bond;
and $R^4$ is combined together with X to represent a single bond, or represents hydrogen, alkanoyl, and the like.

9 Claims, No Drawings

RADICICOL DERIVATIVES

This application is a division of U.S. application Ser. No. 09/513,472 filed Feb. 25, 2000 now U.S. Pat. No. 6,239,168, which in turn is a division of U.S. application Ser. No. 09/091,752, filed Jun. 24, 1998 now U.S. Pat. No. 6,316,491.

TECHNICAL FIELD

The present invention relates to novel radicicol derivatives or pharmacologically acceptable salts thereof which show tyrosine kinase inhibition activity and have antitumor or immunosuppression effects.

BACKGROUND ART

It is known that microbial metabolite radicicol represented by the following formula (B) has an antifungal effect and an anticancer effect [*Nature,* 171, 344 (1953); *Neoplasma,* 24, 21 (1977) ], an immunosuppression effect (Japanese Published Unexamined Patent Application No. 298764/94), or morphology normalization effect of ras or mos canceration cells [*Oncogene,* 11, 161 (1995)].

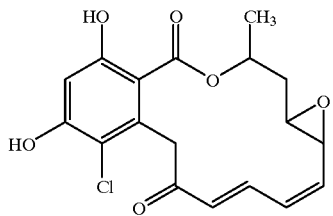

(B)

Furthermore, it is known that radicicol derivatives in which the phenolic hydroxyl group is modified with various acyl groups have an antitumor effect (Japanese Published Unexamined Patent Application No. 226991/92). In addition, it is disclosed that radicicol derivatives in which the phenolic hydroxyl group is modified with an acyl group or an alkyl group show an angiogenesis inhibition effect (Japanese Published Unexamined Patent Application No. 279279/94) or an interleukin 1 production inhibition effect (Japanese Published Unexamined Patent Application No. 40893/96) Recently, oxime derivatives of dienone of a radicicol derivative showing antitumor action and immunosuppression action have been published (WO 96/33989: published on Oct. 31, 1996), and antitumor radicicol derivatives represented by the following formula (B') have also been published (Japanese Published Unexamined Patent Application 202781/97: published on Aug. 5, 1997).

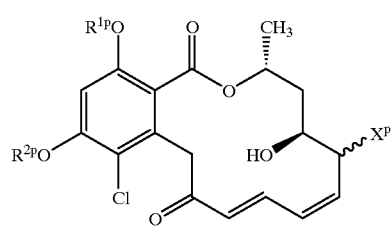

(B')

(In the formula, $R^{1p}$ and $R^{2p}$ represent a hydrogen atom or an acyl group; and $X^p$ represents a halogen atom, a hydroxyl group or a lower alkoxy group.)

Additionally, it is known that ansamycins antibiotics, geldanamycin, represented by formula (C) [*The Journal of Antibiotics,* 23, 442 (1970)] has tyrosine kinase inhibition activity and antitumor effects [for example, *Cancer Research,* 52, 1721 (1992) and *Cancer Research,* 54, 2724 (1994)]. It is shown that these effects are expressed by the inhibition of the activation of a tyrosine kinase, such as Src, ErbB-2, Lck or the like, and a serine/threonine kinase Raf-1, through the formation of a complex of geldanamycin with a molecular chaperone Hsp (heat shock/stress protein) 90 by binding to Hsp90 [for example, *Proceedings of the National Academy of Sciences* of the U.S.A, 91, 8324 (1994) and *The Journal of Biological Chemistry,* 270, 24585 (1995)]. Consequently, drugs capable of acting upon Hsp90 are also included in tyrosine kinase inhibitors and useful not only as antitumor agents but also for the prevention and treatment of various diseases such as osteoporosis, immune diseases, and the like.

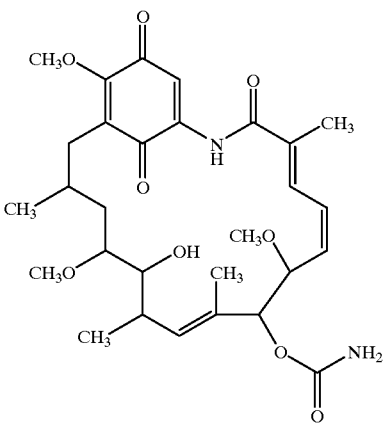

(C)

Tyrosine kinase is an enzyme which uses ATP as a phosphate donor and catalyzes transfer of its γ-phosphate group to the hydroxyl group of a specified tyrosine residue of a substrate protein, thereby taking an important role in the control mechanism of intracellular signal transduction. Various tyrosine kinase families are known. Tyrosine kinase activities, such as Src in colon cancer, ErbB-2 in breast cancer and gastric cancer, Abl in leukemia, and the like, increase. Disordered increase in the tyrosine kinase activity causes abnormal differentiation and proliferation of cells. Consequently, specific inhibitors of tyrosine kinase are useful in preventing and treating various diseases, including as antitumor agents.

Lck is a tyrosine kinase which is activated when T lymphocytes are activated by antigen stimulation, and an inhibitor of this enzyme is useful as an immunosuppressant. Also, it is known that Src relates to bone resorption in osteoclast, and an inhibitor of this tyrosine kinase is useful as a bone resorption inhibitor for the treatment of osteoporosis. Additionally, inhibitors of receptor type tyrosine kinases of various growth factors, such as FGF-R (epidermal growth factor receptor), FGF-R (fibroblast growth factor receptor), PDGF-R (platelet-derived growth factor receptor), and the like, are useful as a solid cancer growth inhibitor, an angiogenesis inhibitor, a vascular smooth muscle growth inhibitor, and the like.

DISCLOSURE OF THE INVENTION

An object of the present invention is to provide novel radicicol derivatives or pharmacologically acceptable salts thereof which show tyrosine kinase inhibition activity and have antitumor or immunosuppression effects.

The present invention can provide radicicol derivatives represented by the following formula (I) or pharmacologically acceptable salts thereof:

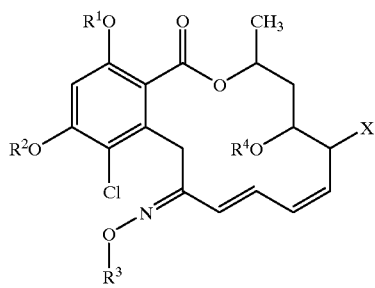

(I)

wherein $R^1$ and $R^2$ are the same or different, and each represents hydrogen, alkanoyl, alkenoyl, tert-butyldiphenylsilyl or tert-butyldimethylsilyl;

$R^3$ represents:

Y—$R^5$ {wherein Y represents substituted or unsubstituted alkylene; and $R^5$ represents CONR$^6$R$^7$ (wherein $R^6$ represents hydrogen, hydroxyl, substituted or unsubstituted lower alkyl, substituted or unsubstituted higher alkyl, substituted or unsubstituted lower cycloalkyl, substituted or unsubstituted alkenyl, substituted or unsubstituted lower alkoxy, substituted or unsubstituted aryl, a substituted or unsubstituted heterocyclic group, or NR$^8$R$^9$ (wherein $R^8$ and $R^9$ are the same or different, and each represents hydrogen, substituted or unsubstituted lower alkyl, substituted or unsubstituted higher alkyl, substituted or unsubstituted lower cycloalkyl, substituted or unsubstituted aryl, a substituted or unsubstituted heterocyclic group, substituted or unsubstituted alkanoyl, substituted or unsubstituted aroyl, carbonyl bound to a substituted or unsubstituted heterocyclic ring, or substituted or unsubstituted arylcarbamoyl), or is combined together with $R^7$ and adjoining N to represent a substituted or unsubstituted heterocyclic group; and $R^7$ is combined together with $R^6$ and adjoining N to represent a substituted or unsubstituted heterocyclic group, or represents hydroxyl, substituted lower alkyl, substituted or unsubstituted higher alkyl, substituted or unsubstituted lower cycloalkyl, substituted or unsubstituted alkenyl, substituted or unsubstituted lower alkoxy, substituted or unsubstituted aryl, a substituted or unsubstituted heterocyclic group, or NR$^{10}$R$^{11}$ (wherein $R^{10}$ and $R^{11}$ have the same meaning as $R^8$ and $R^9$ defined above, respectively)), CO$_2$R$^{12}$ (wherein $R^{12}$ represents substituted lower alkyl, substituted or unsubstituted higher alkyl, substituted or unsubstituted lower cycloalkyl, substituted or unsubstituted alkenyl, substituted or unsubstituted aryl, or a substituted or unsubstituted heterocyclic group), substituted or unsubstituted aryl, substituted or unsubstituted pyridyl, substituted or unsubstituted pyridonyl, substituted or unsubstituted pyrrolidonyl, substituted or unsubstituted uracilyl, substituted or unsubstituted piperidyl, substituted or unsubstituted piperidino, substituted or unsubstituted pyrrolidinyl, substituted or unsubstituted morpholino, substituted or unsubstituted morpholinyl, substituted or unsubstituted piperazinyl, substituted or unsubstituted thiomorpholino, or substituted or unsubstituted dioxolanyl}, COR$^{13}$ (wherein $R^{13}$ represents hydrogen, substituted or unsubstituted lower alkyl, substituted or unsubstituted higher alkyl, substituted or unsubstituted aryl, substituted or unsubstituted lower alkoxy, or NR$^{14}$R$^{15}$ (wherein $R^{14}$ and $R^{15}$ are the same or different, and each represents hydrogen, substituted or unsubstituted-lower alkyl, substituted or unsubstituted higher alkyl, substituted or unsubstituted aryl, or substituted or unsubstituted pyridyl, or $R^{14}$ and $R^{15}$ are combined together with adjoining N to represent a substituted or unsubstituted heterocyclic group)), or substituted or unsubstituted aryl;

X represents halogen, or is combined together with $R^4$ to represent a single bond; and $R^4$ is combined together with X to represent a single bond, or represents hydrogen, alkanoyl, alkenoyl, or —SO—Z {wherein Z represents formula (A):

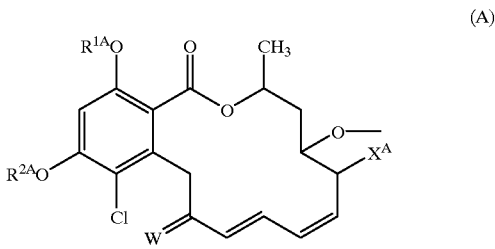

(A)

wherein $R^{1A}$ and $R^{2A}$ have the same meaning as $R^1$ and $R^2$ defined above, respectively; $X^A$ represents halogen; and W represents O or N—O—$R^{3A}$ (wherein $R^{3A}$ has the same meaning as $R^3$ defined above)}.

Hereinafter, the compound represented by formula (I) will be called compound (I). Compounds of other formula numbers with also be called in the same manner.

(1) Explanation of each group

In the definition of each group of compound (I), the term "lower" means 1 to 8 carbon atoms, and the term "higher" means 9 to 30 carbon atoms, unless otherwise indicated.

Examples of the alkanoyl include straight or branched groups having 1 to 30 carbon atoms, such as formyl, acetyl, propanoyl, isopropanoyl, butanoyl, caproyl, lauroyl, myristoyl, palmitoyl, stearoyl, and the like. Examples of the alkenoyl include straight or branched groups having 3 to 30 carbon atoms, such as acryloyl, methacryloyl, crotonoyl, isocrotonoyl, palmitoleoyl, linoleoyl, linolenoyl, and the like. Examples of the alkyl moiety of the lower alkyl and the lower alkoxy include straight or branched groups, such as methyl, ethyl, propyl, isopropyl, butyl, isobutyl, sec-butyl, tert-butyl, pentyl, isopentyl, neopentyl, hexyl, heptyl, octyl, isooctyl, and the like, and one of the carbon atoms thereof may be substituted with a silicon atom. Examples of the higher alkyl include straight or branched groups, such as decanyl, dodecyl, hexadecyl, and the like. Examples of the alkenyl include straight or branched groups having 2 to 30 carbon atoms, such as vinyl, allyl, 1-propenyl, 2-butenyl, 1-pentenyl, 2-hexenyl, 1, 3-pentadienyl, 1, 3-hexadienyl, dodecenyl, hexadecenyl, and the like. Examples of the lower cycloalkyl include groups having 3 to 8 carbon atoms, such as cyclopropyl, cyclobutyl, cyclopentyl, cyclohexyl, cyclooctyl, and the like. Examples of the aryl include phenyl, naphthyl, and the like, and the aryl moiety of aroyl and arylcarbamoyl has the same meaning. Examples of the heterocyclic group include alicyclic heterocyclic groups, aromatic heterocyclic groups, and the like, such as pyridonyl, pyrrolidonyl, uracilyl, dioxolanyl, pyrrolyl, tetrazolyl, pyrrolidinyl, thienyl, morpholino, thiomorpholino, piperazinyl, pyrazolidinyl, piperidino, pyridyl, homopiperazinyl, pyrazolyl, pyrazinyl, indolyl, isoindolyl, furyl, piperidyl, quinolyl, phthalazinyl, imidazolidinyl, imidazolinyl, pyrimidinyl, and the like. The heterocyclic group moiety in the carbonyl bound to a heterocyclic ring has the same meaning as defined above, and examples of the entire group containing carbonyl include furoyl, thenoyl, nicotinoyl, isonicotinoyl, and the like. Examples of the nitrogen containing heterocyclic group formed by $R^6$ and $R^7$ with the adjoining N and the nitrogen containing heterocyclic group formed by $R^{14}$ and $R^{15}$ with the adjoining N (said heterocyclic group may further contain O, S or other N) include pyrrolidyl, morpholino, thiomorpholino, piperazinyl, pyrazolidinyl, pyrazolinyl, piperidino, homopiperazinyl, indolinyl, isoindolinyl, perhydroazepinyl, perhydroazocinyl, indolyl, isoindolyl, and the like. Examples of the alkylene include those groups in which one hydrogen atom is removed from the group of alkyl moiety of the above lower alkyl or higher alkyl. Examples of the halogen include fluorine, chlorine, bromine and iodine atoms.

(2) Explanation of substituent in each group

Examples of the substituent in the substituted lower alkyl, the substituted higher alkyl, the substituted alkenyl, the substituted lower alkoxy and the substituted alkanoyl include 1 to 3 substituents, which are the same or different, such as hydroxyl, lower cycloalkyl, lower cycloalkenyl, lower alkoxy, lower alkanoyloxy, azido, amino, mono- or di-lower alkylamino, mono- or di-lower alkanoylamino, lower alkoxycarbonylamino, lower alkenyloxycarbonylamino, halogen, lower alkanoyl, substituted or unsubstituted aryl, a substituted or unsubstituted heterocyclic group, cyclic imido (a group formed by removing hydrogen bound to an imido N atom), $CONR^{16}R^{17}$ (wherein $R^{16}$ and $R^{17}$ are the same or different, and each represents hydrogen, hydroxyl, lower alkyl, lower cycloalkyl, higher alkyl, alkenyl, lower alkoxy, aryl, a heterocyclic group, or $NR^{18}R^{19}$ (wherein $R^{18}$ and $R^{19}$ are the same or different, and each represents hydrogen, lower alkyl, lower cycloalkyl, aryl, a heterocyclic group, lower alkanoyl, aroyl, carbonyl bound to a heterocyclic ring, or arylcarbamoyl)), $CO_2R^{20}$ (wherein $R^{20}$ represents hydrogen, lower alkyl, higher alkyl, lower cycloalkyl, alkenyl, substituted or unsubstituted aryl, or a substituted or unsubstituted heterocyclic group), or —$(OCH_2CH_2)_nOCH_3$ (wherein n is an integer of 1 to 10).

Examples of the substituent in the substituted alkylene include 1 to 3 substituents, which are the same or different, such as hydroxyl, lower alkoxy, lower alkanoyloxy, azido, amino, mono- or di-lower alkylamino, mono- or di-lower alkanoylamino, lower alkoxycarbonylamino, lower alkenyloxycarbonylamino, halogen, lower alkanoyl, substituted or unsubstituted aryl, substituted or unsubstituted pyridyl, substituted or unsubstituted pyridonyl, substituted or unsubstituted pyrrolidonyl, substituted or unsubstituted uracilyl, substituted or unsubstituted piperidyl, substituted or unsubstituted piperidino, substituted or unsubstituted pyrrolidinyl, substituted or unsubstituted morpholino, substituted or unsubstituted morpholinyl, substituted or unsubstituted piperazinyl, substituted or unsubstituted thiomorpholino, substituted or unsubstituted dioxolanyl, cyclic imido (a group formed by removing hydrogen bound to an imido N atom), $CONR^{16}R^{17}$ (wherein $R^{16}$ and $R^{17}$ have the same meaning as defined above), or $CO_2R^{20}$ (wherein $R^{20}$ has the same meaning as defined above).

Examples of the substituent in the substituted lower cycloalkyl, the substituted aryl, the substituted heterocyclic group, the substituted aroyl, the carbonyl bound to a substituted heterocyclic ring, the substituted arylcarbamoyl, the substituted pyridyl, the substituted pyridonyl, the substituted pyrrolidonyl, the substituted uracilyl, the substituted piperidyl, the substituted piperidino, the substituted pyrrolidinyl, the substituted morpholino, the substituted morpholinyl, the substituted piperazino, the substituted piperazinyl, the substituted thiomorpholino, the substituted dioxolanyl and the substituted nitrogen containing heterocyclic group formed with the adjoining N include 1 to 3 substituents, which are the same or different, such as hydroxyl, lower alkyl, lower alkyl substituted with a heterocyclic ring (said heterocyclic ring may be substituted with lower alkyl), higher alkyl, alkenyl, lower cycloalkyl, lower cycloalkenyl, lower alkoxy, lower alkoxy-lower alkoxy, lower alkanoyloxy, azido, amino, mono- or di-lower alkylamino, mono- or di-lower alkanoylamino, lower alkoxycarbonylamino, lower alkenyloxycarbonylamino, halogen, lower alkanoyl, aryl, a heterocyclic group, cyclic imido (a group formed by removing hydrogen bound to an imido N atom), $CONR^{16}R^{17}$ (wherein $R^{16}$ and $R^{17}$ have the same meaning as defined above), $CO_2R^{20}$ (wherein $R^{20}$ has the same meaning as defined above), or $SO_2NR^{21}R^{22}$ (wherein $R^{21}$ and $R^{22}$ are the same or different, and each represents hydrogen or lower alkyl) The lower alkyl, the higher alkyl, the alkenyl, the lower cycloalkyl, the lower alkoxy, the halogen, the aryl, the aroyl, the arylcarbamoyl, the heterocyclic group, and the carbonyl bound to a heterocyclic ring used herein have the same meaning as defined above. The lower alkyl moieties of the mono- or di-lower alkylamino, the lower alkoxycarbonyl, the lower alkoxycarbonylamino, and the lower alkoxy-lower alkoxy have the same meaning as defined above. The lower alkenyl moiety of the lower alkenyloxycarbonylamino means the above alkenyl group having 2 to 8 carbon atoms, such as vinyl, allyl, 1-propenyl, 2-butenyl, 1-pentenyl, 2-hexenyl, 1,3-pentadienyl, 1,3-hexadienyl, and the like. Examples of the lower cycloalkenyl include those having 4 to 8 carbon atoms, such as 2-cyclopentenyl, 2-cyclohexenyl, 1,3-cyclopentadienyl, and the like. Examples of the lower alkanoyl moiety of the lower alkanoyl, the lower alkanoyloxy and the mono- or di-lower alkanoylamino include straight or branched groups having 1 to 8 carbon atoms, such as formyl, acetyl, propanoyl, isopropanoyl, butanoyl, caproyl, and the like. Examples of the cyclic imido include phthalimido, succinimido, glutarimido, and the like.

As compound (I), compounds in which X is a halogen are preferred, and compounds in which X is combined together with $R^4$ to represent a single bond are also preferred. Among the compounds in which X is combined together with $R^4$ to represent a single bond, compounds in which $R^1$ and $R^2$ are hydrogen are preferred. Among these, compounds in which $R^3$ (wherein $R^3$ has the same meaning as defined above) is Y—$R^5$ (wherein $R^5$ has the same meaning as defined above) are more preferred. Among the compounds in which X is combined together with $R^4$ to represent a single bond, compounds in which $R^1$ and $R^2$ are hydrogen, $R^3$ is Y—$R^5$ (wherein $R^5$ has the same meaning as defined above) and $R^5$ is substituted or unsubstituted aryl, and the like, are most preferred, and among these, compounds in which $R^5$ is pyrrolidonyl are particularly preferred.

The pharmacologically acceptable salts of compound (I) include acid addition salts, metal salts, ammonium salts, organic amine addition salts, amino acid addition salts, and the like. Examples of the acid addition salts include inorganic acid salts (for example, hydrochloride, hydrobromide, sulfate, phosphate, and the like), and organic acid salts (for example, formate, acetate, oxalate, benzoate, methanesulfonate, p-toluenesulfonate, maleate, fumarate, tartrate, citrate, succinate, lactate, and the like). Examples of the metal salts include alkali metal salts (for example, lithium salt, sodium salt, potassium salt, and the like), alkaline earth metal salts (for example, magnesium salt, calcium salt, and the like), aluminum salts, zinc salts, and the like. Examples of the ammonium salts include salts with ammonium, tetramethylammonium, and the like. Examples of the organic amine addition salts include addition salts with morpholine, piperidine, and the like. Examples of the amino acid addition salts include addition salts with glycine, phenylalanine, aspartic acid, glutamic acid, lysine, and the like.

The compound of the present invention is generally prepared using radicicol as a starting material. Compound (I) may contain various stereoisomers, geometric isomers, tautomeric isomers, and the like. All of possible isomers and their mixtures are included in the present invention, and the mixing ratio is not particularly limited.

A production method of compound (I) is described below.

The production method of compound (I) mainly comprises oxime formation (production method 1), acylation/carbamoylation/alkoxycarbonylation (production method 2), alkylation (production method 3), amidation/esterification (production method 4), desilylation (production method 5), halohydrination (production method 6), silylation (production method 7), and acylation (production method 8), and each compound of interest is produced by combining these reaction steps depending on the object.

In the production methods shown below, when a defined group changes under conditions of the employed method or is not fit for carrying out the method, the compound of interest can be prepared using an introduction-elimination method of protecting groups usually used in synthetic organic chemistry [for example, see *Protective Groups in Organic Synthesis*, T. W. Greene, John Wiley & Sons Inc. (1981)]. As occasion demands, the sequence of reaction steps, such as introduction of substituent groups and the like, may be changed.

Production Method 1

Compound (Ia) can be prepared according to following reaction step, by oxime formation of the dienone carbonyl of radicicol, compound (D) which is prepared from radicicol by a known method (Japanese Published Unexamined Patent Application No. 226991/92) or compound (E) which is prepared from radicicol or a radicicol derivative in which one of the phenolic hydroxyl groups is substituted with alkanoyl or alkenoyl in accordance with a known method [for example, *Journal of the American Chemical Society*, 94, 6190 (1972)].

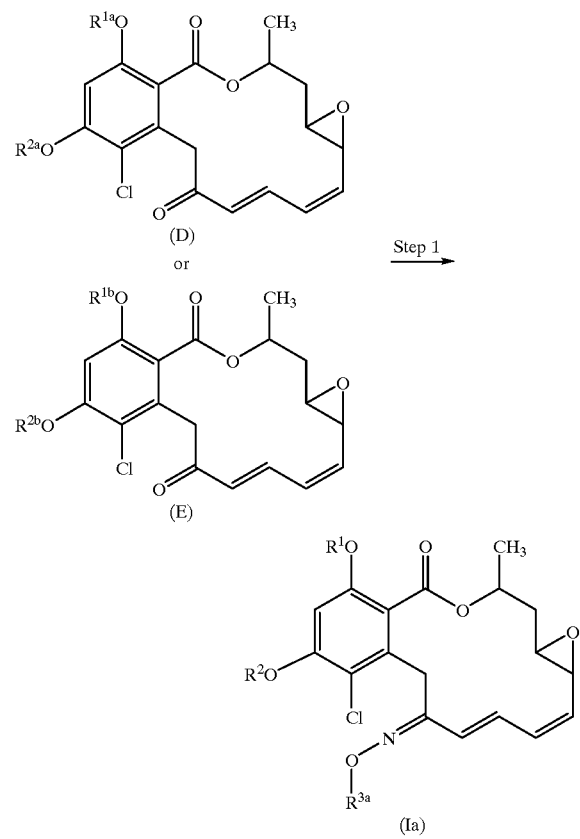

[In the above reaction formula, $R^{1a}$ and $R^{2a}$ represent groups in which tert-butyldimethylsilyl and tert-butyldiphenylsilyl are removed from $R^1$ and $R^2$ described above; $R^{1b}$ and $R^{2b}$ present groups in which at least one of $R^1$ and $R^2$ described above is substituted with tert-butyldimethylsilyl or tert-butyldiphenylsilyl; $R^{3a}$ is a group in which $COR^{13}$ (wherein $R^{13}$ has the same meaning as describe above) is removed from $R^3$ described above; and $R^1$ and $R^2$ have the same meaning as defined above.]

Step 1

Compound (Ia) can be prepared by allowing compound (D) or compound (E) to react with compound (II) represented by the following formula $H_2N$—O—$R^{3a}$ (II) (wherein $R^{3a}$ has the same meaning as defined above) or an acid addition salt thereof.

Examples of the reaction solvent include pyridine, chloroform, dichloromethane, ethyl acetate, ether, tetrahydrofuran (THF), dimethylformamide (DMF), acetonitrile, and the like, which may be used either alone or as a mixture thereof, and pyridine is preferred. Examples of the acid include hydrochloric acid, acetic acid, trifluoroacetic acid, sulfuric acid, p-toluenesulfonic acid, camphorsulfonic acid, and the like, and they are preferably used in an amount of 0.1 to 10 equivalents based on compound (D) or (E). When an acid addition salt of compound (II) is used, the reaction can be carried out in the presence of a base, for example, amines (e.g., pyridine, triethylamine, diisopropylethylamine, N,N-dimethylaniline, N,N-dimethylaniline, or the like) or alkali metal carbonate or bicarbonate (e.g., sodium carbonate, potassium carbonate, or the like), in an amount of 1 equivalent or more based on the acid addition salt of compound (II), preferably using pyridine which also serves as the solvent. The compound (II) or an acid addition salt thereof is used in an amount of 1 equivalent or more, preferably 1 to 5 equivalents, based on compound (D) or (E). The reaction is carried out at a temperature of −20 to 100° C., preferably 20 to 60° C., and the reaction completes after 1 to 80 hours.

Production Method 2

Compound (Ib) can be prepared by the steps in which compound (F) is converted into oxime compound (G), and then the resulting hydroxyl group is subjected to acylation, carbamoylation or alkoxycarbonylation.

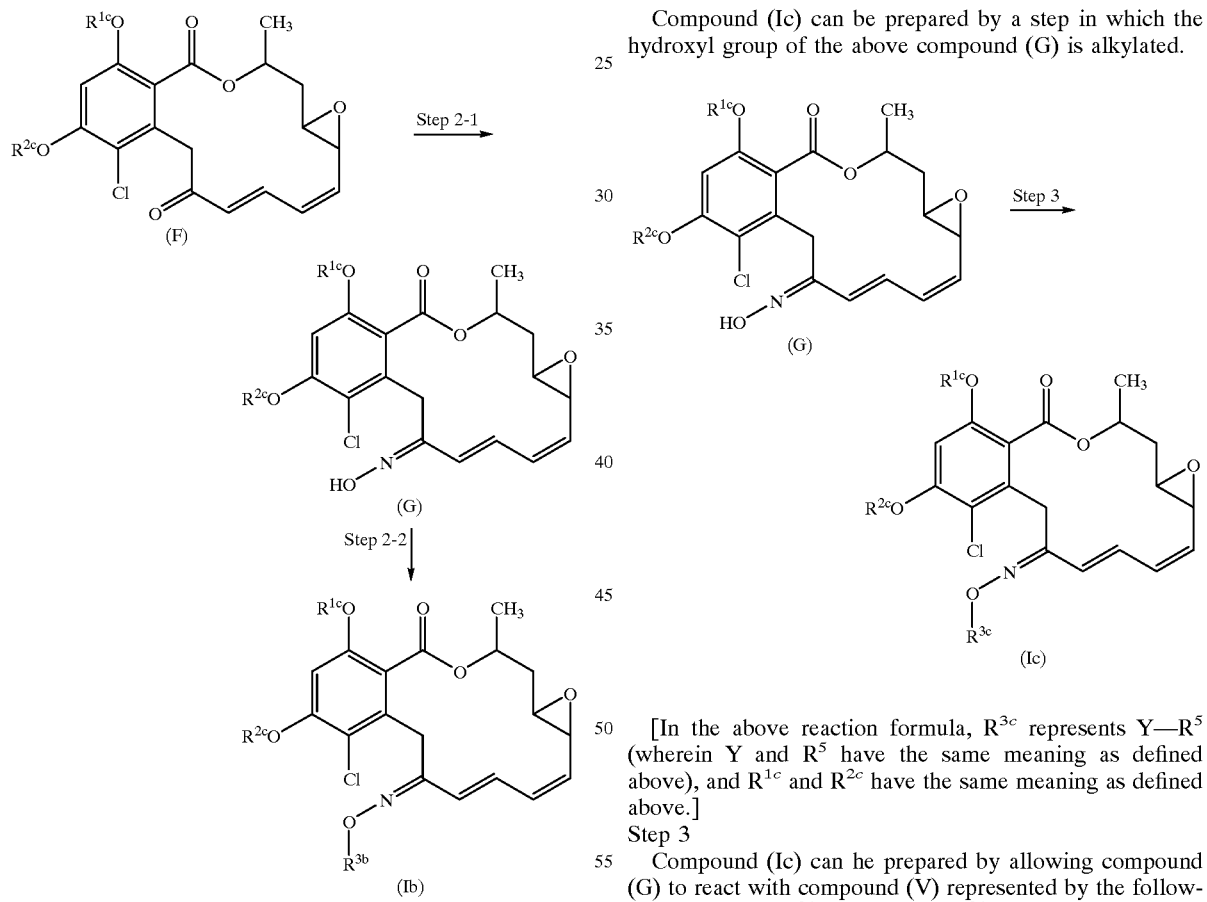

[In the above reaction formula, $R^{1c}$ and $R^{2c}$ are the same or different, and each represents alkanoyl, alkenoyl, tert-butyldimethylsilyl or tert-butyldiphenylsilyl, and $R^{3b}$ represents $COR^{13}$ (wherein $R^{13}$ has the same meaning as defined above).]

Step 2-1

Compound (G) can be prepared by allowing compound (F) to react with hydroxylamine or an acid addition salt thereof according to method of the above step 1.

Step 2-2

Compound (Ib) can be prepared by allowing compound (G) to react with compound (III) represented by the following formula $R^{13}COCl$ (III) (wherein $R^{13}$ has the same meaning as defined above), or with compound (IV) represented by the following formula $R^{23}NCO$ (IV) (wherein $R^{23}$ represents substituted or unsubstituted lower alkyl, substituted or unsubstituted higher alkyl, substituted or unsubstituted aryl, or substituted or unsubstituted pyridyl), in the presence of a base.

As the reaction solvent, dichloromethane, ether, THF, DMF, and the like, may be used alone or as a mixture thereof. As the base, amines (for example, pyridine, triethylamine, diisopropylethylamine, or the like) are used in an amount of 0.1 equivalent or more, preferably 1 to 10 equivalents, based on compound (III) or (IV). Compound (III) or (IV) is used in an amount of 1 equivalent or more, preferably 1 to 5 equivalents, based on compound (G) The reaction is carried out at a temperature of −80 to 100° C., preferably −80 to 0° C., when compound (III) is used, or at a temperature of 0 to 80° C. when compound (IV) is used, and each reaction completes after 10 minutes to 48 hours.

Production Method 3

Compound (Ic) can be prepared by a step in which the hydroxyl group of the above compound (G) is alkylated.

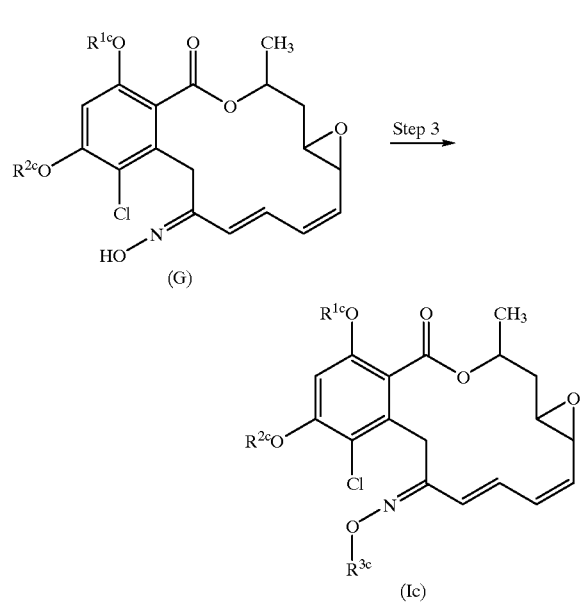

[In the above reaction formula, $R^{3c}$ represents $Y-R^5$ (wherein Y and $R^5$ have the same meaning as defined above), and $R^{1c}$ and $R^{2c}$ have the same meaning as defined above.]

Step 3

Compound (Ic) can be prepared by allowing compound (G) to react with compound (V) represented by the following formula $HOR^{24}$ (V) (wherein $R^{24}$ has the same meaning as $R^{3c}$ defined above) in the presence of a condensing agent.

As the reaction solvent, toluene, dichloromethane, and the like, are used alone or as a mixture thereof. As the condensing agent, trivalent phosphorous compounds (for example, triphenylphosphine, tributylphosphine, or the like) and azo compounds (for example, diethyl azodicarboxylate (DEAD), 1,1-(azodicarbonyl) dipiperidine, and the like) are used as a mixture thereof. Each of compound (V) and the condensing agent is used in an amount of 1 equivalent or more, preferably 1 to 5 equivalents, based on compound (G).

The reaction is carried out at a temperature of −20 to 80° C., preferably 0 to 30° C., and the reaction completes after 5 minutes to 48 hours.

Production Method 4

Compound (Id) can be prepared by steps in which compound (E) is converted into oxime compound (J) in which a carboxyl group is introduced, and then the carboxyl group is subjected to amidation or esterification.

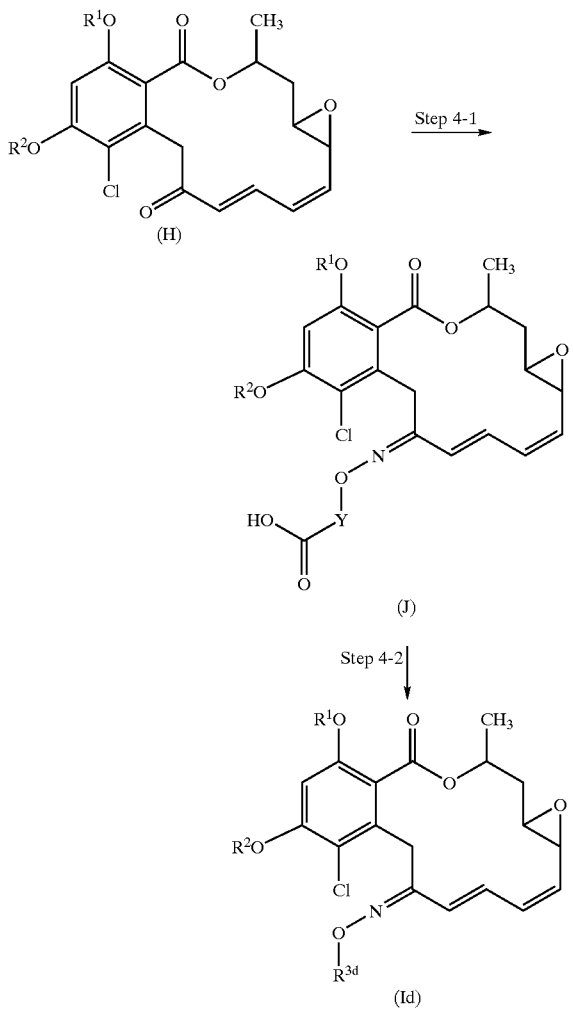

{In the above reaction formula, $R^{3d}$ represents Y—$R^{5a}$ [wherein $R^{5a}$ represents $CONR^6R^7$ (wherein $R^6$ and $R^7$ have the same meaning as defined above) or $CO_2R^{12}$ (wherein $R^{12}$ has the same meaning as defined above), and Y has the same meaning as defined above], and Y, $R^1$ and $R^2$ have the same meaning as defined above.}

Step 4-1

Compound (J) can be prepared by allowing compound (H) to react with compound (VI) represented by the following formula $H_2N$—O—Y—$CO_2H$ (VI) (wherein Y has the same meaning as defined above) or an acid addition salt thereof according to the method of the above step 1.

Step 4-2

Compound (Id) can be prepared by allowing compound (J) to react with compound (VII) represented by the following formula $HNR^6R^7$ (VII) (wherein $R^6$ and $R^7$ have the same meaning as defined above) or an acid addition salt thereof, or with a compound (VIII) represented by the following formula $HOR^{12}$ (VIII) (wherein $R^{12}$ has the same meaning as defined above), in the presence of a condensing agent.

As the condensing agent, 1-(3-dimethylaminopropyl)-3-ethylcarbodiimide hydrochloride (EDCI), N,N'-dicyclohexylcarbodiimide (DCC), 1,1'-carbonyldiimidazole, or the like, is used. Additionally, the reaction can be accelerated by adding an additive agent, such as N-hydroxysucciniimide (HONSu), 4-(dimethylamino) pyridine (DMAP), 1-hydroxybenzotriazole hydrate (HOBt), or the like, in an amount of 0.1 to 5 equivalents based on compound (J) As the reaction solvent, dichloromethane, ether, THF, DMF, and the like, may be used alone or as a mixture thereof. When an acid addition salt of compound (VII) is used, the reaction can be carried out in the presence of a base, such as amines (for example, pyridine, triethylamine, diisopropylethylamine, or the like), preferably triethylamine, in an amount of 1 equivalent or more, preferably 1 to 10 equivalents, based on the acid addition salt of compound (VII). Each of compound (VII) or an acid addition salt thereof or compound (VIII) and the condensing agent is used in an amount of 1 equivalent or more, preferably 1 to 5 equivalents, based on compound (J) The reaction is carried out at a temperature of −20 to 80° C., preferably 0 to 40° C., and each reaction completes after 10 minutes to 48 hours.

Production Method 5

Compound (If) can be prepared by carrying out desilylation of compound (Ie) which is a derivative compound of (I) in which at least one of $R^1$ and $R^2$ is substituted with tert-butyldimethylsilyl or tert-butyldiphenylsilyl.

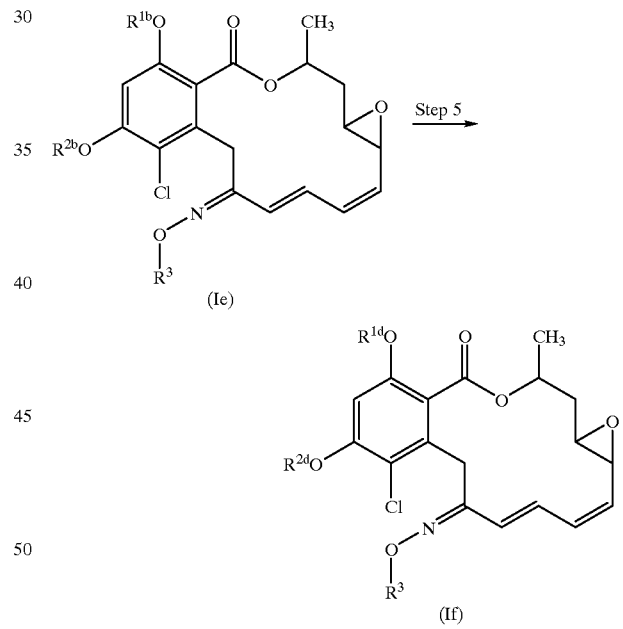

(In the above reaction formula, $R^{1b}$, $R^{2b}$ and $R^3$ have the same meaning as defined above, and $R^{1d}$ and $R^{2d}$ are groups in which at least one of tert-butyldimethylsilyl or tert-butyldiphenylsilyl of the above $R^{1b}$ and $R^{2b}$ is substituted with hydrogen.)

Step 5

Compound (If) can be prepared by allowing compound (Ie) to react with a desilylation agent.

As the reaction solvent, THF, chloroform, dichloromethane, toluene, water, methanol, and the like may be used alone or as a mixture thereof. Examples of the desilylation agent include tetrabutylammonium fluoride (TBAF), sodium fluoride, hydrofluoric acid, and the like.

The reaction may be carried out by increasing the reaction pH by adding an acid, such as acetic acid, hydrochloric acid or the like. The desilylation agent is used in an amount of 0.1 equivalent or more, preferably 1 to 10 equivalents, based on compound (Ie). The reaction is carried out at a temperature of −20 to 50° C., and the reaction completes after 5 minutes to 24 hours.

Production Method 6

Compound (Ih) can be prepared by ring-opening the epoxide of compound (Ig) into a halohydrin or the like.

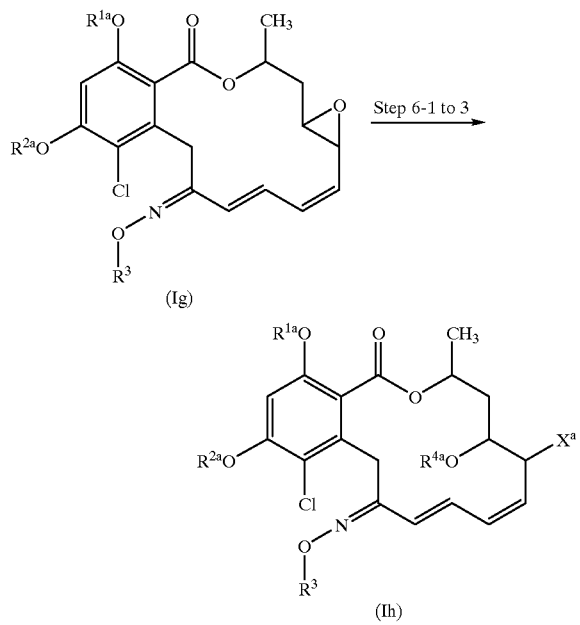

[In the above reaction formula, $R^{1a}$, $R^{2a}$ and $R^3$ have the same meaning as defined above; $X^a$ represents halogen; and $R^{4a}$ represents hydrogen, formyl, or —SO—Z (wherein Z has the same meaning as defined above).]

Step 6-1

A member of compound (Ih) in which $R^{4a}$ is hydrogen can be prepared by allowing compound (Ig) to react with an acid (for example, hydrogen chloride, hydrogen bromide, or the like) or a Lewis acid (for example, titanium tetrachloride, or the like).

As the solvent, dioxane, THF, ether, chloroform, dichloromethane, DMF, acetonitrile, methanol, ethyl acetate, and the like may be used either alone or as a mixture thereof. The acid or Lewis acid is used in an amount of 1 equivalent or more, preferably 1 to 10 equivalents, based on compound (Ig). The reaction is carried out at a temperature of −20 to 40° C., preferably 0 to 40° C., and the reaction completes after 10 minutes to 48 hours.

Step 6-2

A member of compound (Ih) in which $R^{4a}$ is formyl can be prepared by allowing compound (Ig) to react with phosphorous oxychloride or phosphorous oxybromide in DMF. Phosphorous oxychloride or phosphorous oxybromide is used in an amount of 1 equivalent or more, preferably 2 to 5 equivalents, based on compound (Ig). The reaction is carried out at a temperature of −10 to 40° C., preferably 0 to 40° C., and the reaction completes after 1 to 48 hours.

Step 6-3

A dimer compound as a member of compound (Ih) in which $R^{4a}$ is —SO—Z (wherein Z has the same meaning as defined above) can be prepared by allowing compound (Ig) to react with thionyl chloride or thionyl bromide. As the solvent, DMF, chloroform, dichloromethane, dimethyl sulfoxide (DMSO), acetonitrile, and the like may be used either alone or as a mixture thereof. Thionyl chloride or thionyl bromide is used in an amount of 1 equivalent or more, preferably 2 to 10 equivalents, based on compound (Ig). The reaction is carried out at a temperature of −10 to 40° C., preferably 0 to 40° C., and the reaction completes after 1 to 48 hours.

Production Method 7

Compound (Ij) which is a derivative of compound (I) in which at least one of $R^1$ and $R^2$ is substituted with tert-butyldimethylsilyl or tert-butyldiphenylsilyl can be prepared from compound (Ii) by the following step.

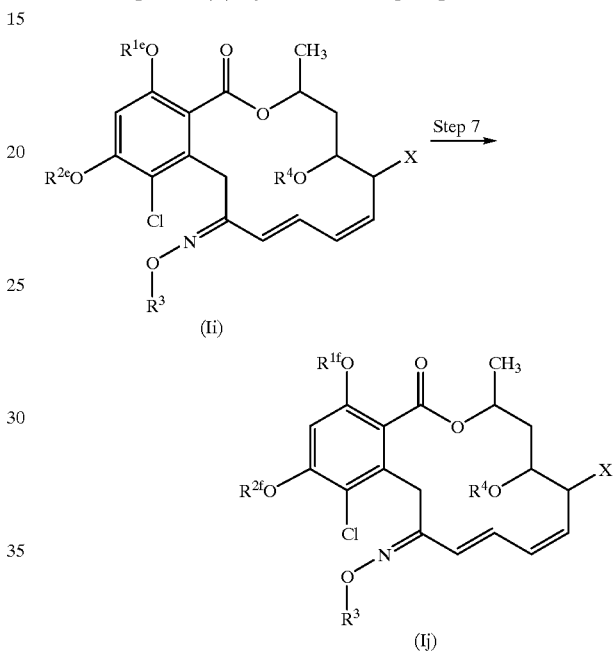

(In the above reaction formula, $R^3$, $R^4$, and X have the same meaning as defined above; $R^{1e}$ and $R^{2e}$ represent both hydrogen, or one represents hydrogen and the other represents alkanoyl or alkenoyl; and $R^{1f}$ and $R^{2f}$ represent groups in which at least one hydrogen of either of the above $R^{1e}$ and $R^{2e}$ is substituted with tert-butyldimethylsilyl or tert-butyldiphenylsilyl.)

Step 7

Compound (Ij) can be prepared by allowing compound (Ii) to react with tert-butyl(chloro)dimethylsilane or tert-butylchlorodiphenylsilane in the presence of a base.

As the solvent, chloroform, dichloromethane, ether, THF, acetone, DMF, acetonitrile, and the like are used either alone or a mixture thereof. As the base, amines (for example, pyridine, imidazole, triethylamine, diisopropylethylamine, or the like) are used. Tert-butyl(chloro)dimethylsilane or tert-butylchlorodiphenylsilane is used in an amount of 1 equivalent or more, preferably 1 to 10 equivalents, based on compound (Ii). The base is used in an amount of 1 equivalent or more, preferably 1 to 10 equivalent, based on tert-butyl (chloro)dimethylsilane or tert-butylchlorodiphenylsilane. The reaction is carried out at a temperature of −20 to 50° C., preferably 10 to 40° C., and the reaction completes after 10 minutes to 24 hours.

Production Method 8

Compound (Im) in which at least one hydrogen of any one of $R^1$, $R^2$ and $R^4$ in compound (I) is substituted with alkanoyl or alkenoyl can be prepared by carrying out acylation of the following compound (Ik).

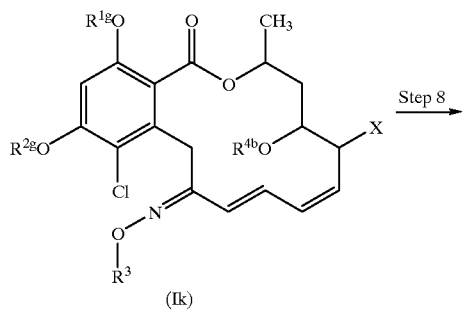

(Ik)

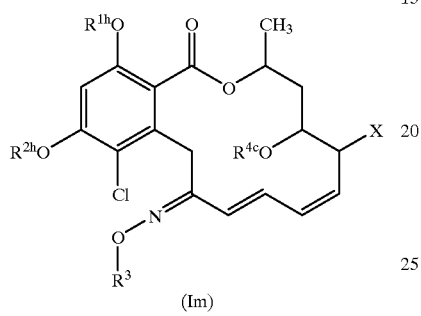

(Im)

(In the above reaction formula, $R^3$ and X have the same meaning as defined above; at least one of $R^{1g}$, $R^{2g}$ and $R^{4b}$ represents hydrogen; and $R^{1h}$, $R^{2h}$ and $R^{4c}$ represent groups in which at least one hydrogen of the above $R^{1g}$, $R^{2g}$ and $R^{4b}$ is substituted with alkanoyl or alkenoyl.)

Step 8

Compound (Im) can be prepared by allowing compound (Ik) to react with 1 equivalent or more, preferably 1 to 100 equivalents, of an acid halide, an acid anhydride, a mixed acid anhydride containing the alkanoyl or alkenoyl of interest, or the like, in the presence of a base.

As the solvent, DMF, DMSO, chloroform, dichloromethane, toluene, and the like may be used either alone or as a mixture thereof. An optional hydroxyl group can be modified by optionally carrying out introduction and elimination of a protecting group of the hydroxyl group, and it is possible to modify a plurality of hydroxyl groups at the same time. As the base, pyridine, triethylamine, N,N-dimethylaniline, N,N-dimethylaniline, or the like is used in an amount of 1 equivalent or more, preferably 1 to 200 equivalents, based on compound (Ik). It is possible to use a base (for example, pyridine, or the like) also as the solvent. Additionally, the reaction can be accelerated by adding DMAP or the like in an amount of 0.1 to 4 equivalents based on compound (Ik). The reaction is carried out at a temperature of −20 to 50° C., and the reaction completes after 5 minutes to 24 hours.

In the production of compound (I), conversion of the functional group of $R^1$, $R^2$, $R^3$, $R^4$ or X can be carried out not only by the above steps but also by known methods [for example, *Comprehensive Organic Transformations*, R. C. Larock (1989)].

Isolation and purification of the products of the above methods can be carried out by carrying out optional combinations of techniques generally used in organic syntheses (e.g., filtration, extraction, washing, drying, concentration, crystallization, various types of chromatography, and the like). The intermediates may be used in the subsequent reactions without purification.

If a salt of compound (I) is prepared, the salt of compound (I) can be purified as such when it can be prepared; or, when the compound is prepared in its free form, its salt can be formed by dissolving or suspending it in an appropriate solvent and adding an acid or base thereto.

Also, compound (I) or pharmacologically acceptable salts thereof may exist in the form of addition products with water or various solvents, and these addition products are also included in the present invention. Examples of compound (I) are shown in Table 1.

TABLE 1

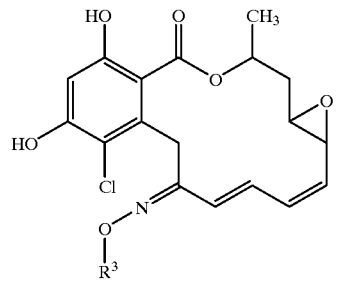

(1) Specific examples of compound (I)

| Compound | $R^3$ |
|---|---|
| 1 | ![CH2CON-piperidine] CH$_2$CON⟨piperidinyl⟩ |
| 2 | CH$_2$CON⟨pyrrolidinyl⟩ |
| 3 | CH$_2$CON⟨morpholinyl⟩ |
| 4 | CH$_2$CON⟨piperazinyl⟩NCH$_3$ |
| 5 | CH$_2$CONH(CH$_2$)$_2$N(CH$_2$CH$_3$)$_2$ |
| 6 | CH$_2$CONH(CH$_2$)$_2$OH |
| 7 | CH$_2$CON[(CH$_2$)$_2$OH]$_2$ |
| 8 | CH$_2$CONHCH$_2$CO$_2$CH$_3$ |
| 9 | CH$_2$CONHNH$_2$ |
| 10 | CH$_2$CONHNHCONHC$_6$H$_5$ |
| 11 | CH$_2$CON⟨azepanyl⟩ |
| 12 | CH$_2$CON⟨piperidinyl-CH$_3$⟩ |
| 13 | CH$_2$CON⟨piperidinyl-OH⟩ |

TABLE 1-continued

[Structure: macrocyclic compound with HO, Cl, oxime O-R³ substituents, epoxide, and ester linkages]

| Compound | R³ |
|---|---|
| 14 | CH₂CON(piperidinyl-piperidine) |
| 15 | CH₂CON(piperidine-4-carboxamide) |
| 16 | CH₂CONH(CH₂)₉CH₃ |

(2) Specific examples of compound (I)

| Compound | R³ |
|---|---|
| 17 | CH₂CONH-CH₂CH₂CH₂-Cl |
| 18 | CH₂CONH-CH₂CH₂-OCH₂CH₃ |
| 19 | CH₂CONH-CH₂-CH=CH₂ |
| 20 | CH₂CONH-CH₂-cyclohexyl |
| 21 | CH₂CONH-CH₂-(3,4,5-trimethoxyphenyl) |
| 22 | CH₂CONH-CH₂-(3-pyridyl) |
| 23 | CH₂CONH-CH₂CH₂-(N-methylpyrrol-2-yl) |
| 24 | CH₂CONH-CH₂CH₂-piperidinyl (major) |

TABLE 1-continued

[Structure: macrocyclic compound with HO, Cl, oxime O-R³ substituents, epoxide, and ester linkages]

| Compound | R³ |
|---|---|
| 25 | CH₂CONH-CH₂CH₂-piperidinyl (minor) |
| 26 | CH₂CONH-CH₂CH₂CH₂-(2-oxopyrrolidin-1-yl) |
| 27 | CH₂CONH-cyclopentyl |
| 28 | CH₂CONHC₆H₅ |
| 29 | CH₂CONH-(4-isopropylphenyl) |
| 30 | CH₂CONH-(4-methoxyphenyl) |
| 31 | CH₂CONH-(4-diethylaminophenyl) |
| 32 | CH₂CONH-(3-pyridyl) |

(3) Specific examples of compound (I)

| Compound | R³ |
|---|---|
| 33 | CH₂CONHN(CH₃)₂ |
| 34 | CH₂CON(NH₂)-CH₂CH₂OH |
| 35 | CH₂CONHNHC₅H₆ |
| 36 | CH₂CONHNH-(2-pyridyl) |

TABLE 1-continued

[Structure: macrocyclic compound with HO, O, CH₃, HO, Cl, N-O-R³ substituents]

| Compound | R³ |
|---|---|
| 37 | CH₂CONH-N(piperidine) |
| 38 | CH₂CONH-N(piperazine)NCH₃ |
| 39 | (CH₂)₇CON(piperidine) |
| 40 | (CH₂)₁₀CON(piperidine) |
| 41 | CH₂CO₂(CH₂CH₂O)₅CH₃ |
| 42 | CH₂CO₂(CH₂CH₂O)₃CH₃ |
| 43 | CH₂-phenyl |
| 44 | CH₂-(2-hydroxyphenyl) |
| 45 | CH₂-(3,5-dihydroxyphenyl) |
| 46 | CH₂-(3,4,5-trimethoxyphenyl) |

TABLE 1-continued

[Structure: macrocyclic compound with HO, O, CH₃, HO, Cl, N-O-R³ substituents]

| Compound | R³ |
|---|---|
| 47 | CH₂-(3,5-diaminophenyl) |
| 48 | (CH₂)₃-(4-N(CH₃)₂-phenyl) |

(4) Specific examples of compound (I)

| Compound | R³ |
|---|---|
| 49 | CH₂-(4-(N-methylpiperazinylmethyl)phenyl) |
| 50 | CH₂-(2-SO₂N(CH₃)₂-phenyl) |
| 51 | CH₂-(2-pyridyl) |
| 52 | CH₂-(3-pyridyl) (major) |
| 53 | CH₂-(3-pyridyl) (minor) |
| 54 | CH₂-(4-pyridyl) |
| 55 | (CH₂)₃-(3-pyridyl) |

TABLE 1-continued
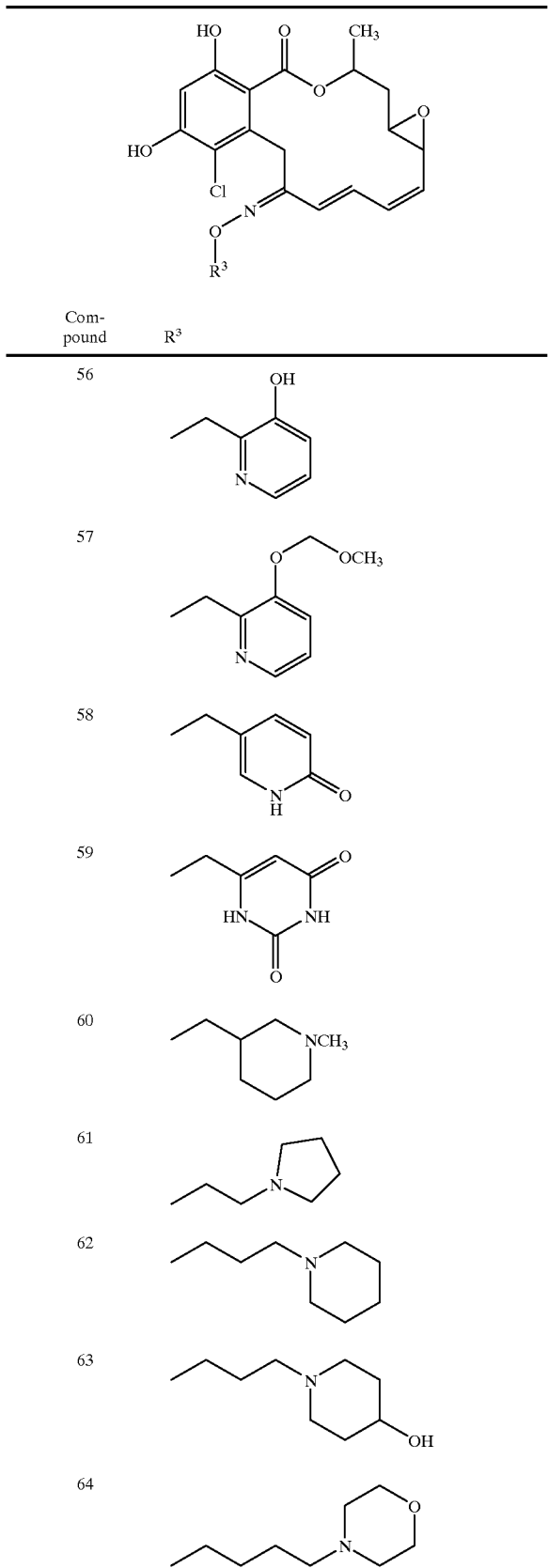
| Compound | R³ |
|---|---|
| 56 | |
| 57 | |
| 58 | |
| 59 | |
| 60 | |
| 61 | |
| 62 | |
| 63 | |
| 64 | |
TABLE 1-continued
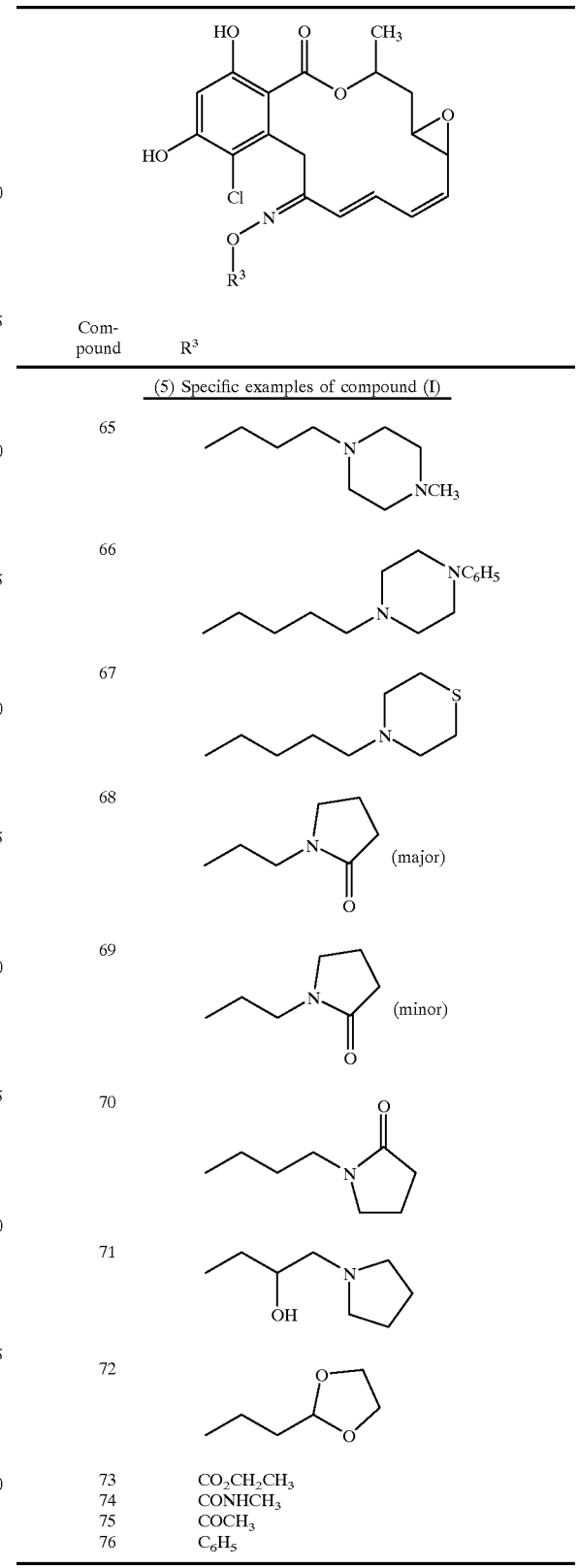
(5) Specific examples of compound (I)
| Compound | R³ |
|---|---|
| 65 | |
| 66 | |
| 67 | |
| 68 | (major) |
| 69 | (minor) |
| 70 | |
| 71 | |
| 72 | |
| 73 | $CO_2CH_2CH_3$ |
| 74 | $CONHCH_3$ |
| 75 | $COCH_3$ |
| 76 | $C_6H_5$ |
Next, pharmacological activities of typical examples of compound (I) are described by the following test examples.

TEST EXAMPLE 1

Inhibition Test of Intracellular Tyrosine Kinase:

SR-3Y1 cells were cultured at 37° C. for 15 hours in an atmosphere of 5% carbon dioxide, using Dulbecco's modified Eagle's medium (DMEM) containing 10% fetal calf serum (FCS), to which each radicicol derivative to be tested had been added in varied concentration. The thus cultured cells were lysed at 4° C. for 20 minutes in a cooled buffer for lysis use (50 mM Tris HCl, pH 7.5, 150 mM sodium chloride (NaCl), 1% Triton X-100, 0.1% sodium dodecyl sulfate (SDS), 1% sodium deoxycholate, 2 mM ethylenediaminetetraacetic acid (EDTA), 1 mM phenylmethanesulfonyl fluoride (PMSF), 20 $\mu$M leupeptin, 0.15 unit/ml aprotinin, 1 mM sodium orthovanadate ($Na_3VO_4$) and then centrifuged at 20,000 G for 30 minutes. After measuring protein concentration in the resulting supernatant fluid, samples were adjusted to the same protein quantity per lane to carry out separation of protein by SDS-PAGE. The thus separated protein samples were transferred onto a nitrocellulose membrane to which were subsequently added a mouse polyclonal phosphotyrosine antibody MX-pTYR (Kyowa Medex Co., Ltd.) as a first antibody and a horseradish peroxidase-conjugated mouse IgG antibody (BIO-RAD Co.) as a second antibody, thereby reacting them with the protein samples on the membrane. Detection was carried out using ECL reagent (Amersham Co.), and the amount of tyrosine-phosphorylated protein was determined by scanning the density of bands prepared on an X-ray film. The activity of radicicol derivatives to inhibit tyrosine phosphorylation can be shown as a concentration ($IC_{50}$) of each derivative by which the ratio of tyrosine-phosphorylated protein is reduced to half in comparison with a control to which the drug is not added.

The results are shown in Table 2.

TABLE 2

Inhibitory activity of intracellular tyrosine kinase

| Compound | $IC_{50}$ ($\mu$M) |
|---|---|
| Radicicol | 0.37 |
| 1 | 0.02 |
| 3 | 0.21 |
| 73 | 0.13 |

According to Table 2, the test compounds show clearly stronger action to inhibit intracellular tyrosine kinase activity than radicicol, and therefore, compound (I) is useful as a tyrosine kinase inhibitor.

TEST EXAMPLE 2

Inhibition Test on the Growth of Rat Normal Fibroblast Cell Line 3Y1-B and its v-src Oncogene Transformed Cell Line SR-3Y1:

The cells were inoculated into a 96 well microplate (# 167008, manufactured by Nunc) in an amount of 1,000 cells per well and pre-cultured at 37° C. for 24 hours in a 5% carbon dioxide gas incubator using Dulbacco's modified Eagle's medium (DMEM) which had been supplemented with 10% fetal calf serum (FCS). Next, a DMSO solution of each test compound which had been adjusted to 10 mM was serially diluted with the culturing medium and add to the wells in 50 $\mu$l portions. Thereafter, the culturing was continued at 37° C. for 72 hours in the 5% carbon dioxide gas incubator. Five hours before completion of the culturing, 3-(4,5-dimethylthiazo-2-yl)-2,5-diphenyltetrazolium bromide (manufactured by Sigma, hereinafter referred to as "MTT") which had been dissolved in the culturing medium to a final concentration of 1 mg/$\mu$l was dispensed into the wells in 50 $\mu$l portions. After completion of the culturing, DMSO was dispensed into the wells in 150 ml portions, and the plate was vigorously stirred using a plate mixer to dissolve MTT-formazan crystals completely. Thereafter, absorbance at 550 nm was measured using a microplate reader MTP-32 (manufactured by Corona Denki). The cell growth inhibition activity was expressed by 50% inhibition concentration ($IC_{50}$).

The results are shown in Table 3.

TABLE 3

Growth inhibition activity upon rat normal fibroblast cell line 3Y1-B and its v-src oncogene transformed cell line SR-3Y1

| | Growth inhibition activity $IC_{50}$ ($\mu$M) | |
|---|---|---|
| Compound | 3Y1-B | SR-3Y1 |
| Radicicol | 0.780 | 0.042 |
| 1 | 0.008 | <0.004 |
| 21 | 0.032 | 0.018 |
| 27 | 0.041 | 0.010 |
| 44 | 0.069 | 0.012 |
| 50 | 0.120 | 0.021 |
| 53 | 0.008 | <0.004 |
| 55 | 0.009 | <0.004 |
| 67 | 0.140 | 0.018 |
| 69 | 0.008 | 0.004 |
| 72 | 0.055 | 0.010 |
| 74 | 0.072 | 0.027 |
| 76 | 0.110 | 0.026 |

According to Table 3, the test compounds showed stronger cell growth inhibition activity upon SR-3Y1 than that upon 3Y1-B and stronger cell growth inhibition activity than that of radicicol upon SR-3Y1. Because of these results, compound (I) is useful as an antitumor agent.

TEST EXAMPLE 3

Antitumor Test on Nude Mouse-Transplanted Human Breast Cancer MX-1 Solid Tumor:

From a tumor lump of a human breast cancer cell line MX-1 subcultured in nude mice (BALB/c nu/nu mice: CLEA Japan), a portion showing good growth was selected and cut into a 2 mm square fragment which was then transplanted under the abdominal side skin of each male nude mouse of 7 to 9 weeks of age using a trocar. The tumor size was measured on the 13th day after the tumor transplantation to select properly growing tumors having a tumor volume of 100 to 300 $mm^3$ (calculated by a calculation formula of "major axis×minor axis$^2$×½"), the mice were optionally grouped into 5 animals per group, and then each test compound which had been dissolved in a 7.5% cremohor EL (manufactured by Sigma)/5% dimethylacetamide (DMA)/87.5% physiological saline solution was administered to the mice by intravenous injection at a dosage of 0.05 ml (100 mg/kg) per day, once a day for 5 days. The antitumor activity of each test compound was expressed by a ratio (T/C) of the tumor volume (T) in the test drug-administered group to the tumor volume (C) in the control group on the 12th or 14th day after administration of the test compound.

The results are shown in Table 4.

TABLE 4

Antitumor activity against human breast cancer
MX-1 solid tumor inoculated in nude mouse

| Compound | T/C (%) | Day measured (after administration of test compound) |
|---|---|---|
| 1 | 3 | 14 |
| 51 | 33 | 14 |
| 53 | 46 | 12 |
| 69 | 4 | 12 |

According to Table 4, the test compounds show excellent antitumor activity, and therefore, compound (I) is useful as an antitumor agent.

TEST EXAMPLE 4
Effect of Decreasing Intracellular Raf-1 Protein Quantity and Erk2 Phosphorylation Inhibition Activity:

Activated K-Ras gene-introduced rat kidney epithelial cell line KNRK 5.2 was cultured at 37° C. for 40 hours in an atmosphere of 5% carbon dioxide gas using Dulbecco's modified Eagle's medium (DMEM) which was supplemented with 10% fetal calf serum (FCS) and to which was added each radicicol derivative at respective test concentration. The resulting cells were lysed for 30 minutes at 4° C. in a cooled buffer for lysis use [50 mM HEPES NaOH, pH 7.4, 250 mM sodium chloride (NaCl), 1 mM ethylenediaminetetraacetic acid (EDTA), 1% Nonidet P-40 (NP40), 1 mM dithiothreitol (DTT), 1 mM phenylmethylsulfonyl fluoride (PMSF), 5 µg/ml leupeptin, 2 mM sodium orthovanadate ($Na_3VO_4$), 1 mM sodium fluoride (NaF), 10 mM β-glycerophosphate] and then centrifuged at 30,000 G for 10 minutes. The protein content of the thus prepared supernatant fluids was measured to prepare samples having the same protein quantity for each lane, and then separation of proteins was carried out by SDS-PAGE. The thus separated protein samples were transferred on a polyvinylidene difluoride (PVDF) membrane, and then anti-phosphorylation MAPK antibody (anti-phospho MAPK, manufactured by New England Biolabs), anti-Erk2 antibody (anti-Erk2, manufactured by Upstate Biotechnology) and anti-Raf-1 antibody (anti-Raf-1 (C-12), manufactured by Santa Cruz Biotechnology) were added thereto as primary antibodies and allowed to react with the proteins on the membrane. Thereafter, a horseradish peroxidase-labeled secondary antibody (anti-rabbit Ig antibody or anti-mouse Ig antibody, manufactured by Amersham) capable of reacting with respective primary antibodies was added thereto as the secondary antibody to carry out the reaction. Detection was carried out using ECL reagent (manufactured by Amersham), and the amount of phosphorylated Erk2 protein, total Erk2 protein and Raf-1 protein was determined by carrying out density scanning of the bands generated on the X-ray film. The Erk2 phosphorylation inhibition activity of radicicol derivatives is determined by calculating the ratio of phosphorylated Erk2 protein (phosphorylated Erk2 protein/total Erk2 protein) based on the results prepared from the samples of respective drug concentrations, which is expressed as the concentration of each derivative ($IC_{50}$) by which the ratio becomes half in comparison with the case in which the drug is not added. Also, the Raf-1 protein decreasing action is examined by calculating the ratio of Raf protein to the amount of Erk2 protein which does not cause changes in the protein quantity by the drug-treatment (Raf-1 protein/total Erk2 protein) based on the results prepared from the samples having respective drug concentrations, which is expressed as the concentration of each derivative ($IC_{50}$) by which the ratio becomes half in comparison with the case in which the drug is not added.

The results are shown in Table 5.

TABLE 5

Effect of decreasing intracellular Raf-1 protein quantity
and Erk2 phosphorylation inhibition activity

| Compound | Raf-1 protein quantity decrease: $IC_{50}$ (µM) | Erk2 phosphorylation inhibition: $IC_{50}$ (µM) |
|---|---|---|
| 50 | 0.34 | 0.35 |
| 53 | 0.38 | 0.07 |
| 64 | 0.19 | 0.11 |
| 69 | 0.12 | 0.06 |

According to Table 5, the test compounds showed effect of decreasing intracellular Raf-1 protein quantity and Erk2 phosphorylation inhibition activity.

Compound (I) or a pharmacologically acceptable salt thereof is administered orally or parenterally as it is or in the form of a pharmaceutical composition. Examples of the dosage form of such a pharmaceutical composition include tablets, pills, powders, granules, capsules, suppositories, injections, drip infusions, and the like.

These dosage forms can be prepared by employing generally known methods and may contain various fillers, lubricants, binders, disintegrators, suspending agents, tonicity agents, emulsifying agents, absorption enhancers, and the like.

Examples of carriers to be used in the pharmaceutical composition include water, distilled water for injection use, physiological saline, glucose, fructose, sucrose, mannitol, lactose, starch, corn starch, cellulose, methyl cellulose, carboxymethyl cellulose, hydroxypropyl cellulose, alginic acid, talc, sodium citrate, calcium carbonate, calcium hydrogenphosphate, magnesium stearate, urea, silicone resin, sorbitan fatty acid ester, glycerol fatty acid ester and the like, which may be optionally selected according to the kind of the pharmaceutical preparation.

Although the dosage and the number of administration times for the purposes may vary depending on the intended therapeutic effect, administration method, treating period, age, body weight, and the like, it may, be administered generally in a dose of 0.01 to 5 mg/kg per day per adult.

BEST MODE OF CARRYING OUT THE INVENTION

Examples and Reference Examples are shown below. The NMR data shown in Examples and Reference Examples are values obtained by measuring at 270 MHz, and the number of protons observed, multiplicity and coupling constant (unit, Hz) are shown in that order in parentheses after the δ value of each signal.

TBS and Boc shown in the following structural formulae and Tables mean tert-butyldimethylsilyl and tert-butoxycarbonyl, respectively.

EXAMPLE 1

Compound 1:
(1-1):

A 1.50 g (4.11 mmol) portion of radicicol was dissolved in 5 ml of pyridine, and the solution was mixed with 1.00 g (9.15 mmol) of aminooxyacetic acid hemihydrochloride and stirred at room temperature for 20 hours and then at 60° C. for 1.5 hours. The solvent was evaporated under reduced pressure, and the resulting residue was purified by silica gel column chromatography (chloroform/methanol=49/1) to obtain 692 mg (yield, 38%) of a compound (K). The thus prepared compound (K) was found to be a mixture of oxime-based isomers (about 3:1) according to $^1$H—NMR.
FAB-MS m/z: 438 [M+H]$^+$
Major component: $^1$H—NMR (CD$_3$OD) δ(ppm): 7.27 (1H, dd, 16.1, 11.2 Hz), 6.82 (1H, d, 16.1 Hz), 6.42 (1H, s), 6.17 (1H, dd, 11.2, 10.5 Hz), 5.61 (1H, dd, 10.5, 3.4 Hz), 5.31 (1H, m), 4.64 (2H, m), 3.91 (1H, d, 16.4 Hz), 3.82 (1H, d, 16.4 Hz), 3.34 (1H, m), 3.02 (1H, m), 2.42 (1H, m), 1.60 (1H, ddd, 14.4, 9.0, 4.2 Hz), 1.53 (3H, d, 6.6 Hz).

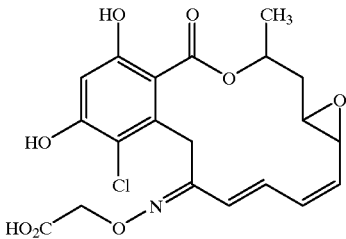

(K)

(1-2):

A 230 mg (0.525 mmol) portion of compound (K) was dissolved in 3 ml of DMF, and the solution was mixed with 121 mg (0.788 mmol) of HOBt, 151 mg (0.788 mmol) of EDCI and 0.078 ml (0.788 mmol) of piperidine and stirred at room temperature for 23 hours and 40 minutes. The reaction solution was mixed with a 0.01 M phosphate buffer of pH 7 and then extracted with ethyl acetate. The ethyl acetate layer was washed with saturated brine and dried with anhydrous sodium sulfate, and then the solvent was evaporated under reduced pressure. The resulting residue was purified by silica gel column chromatography (chloroform/methanol=50/1) to obtain 63.6 mg (yield, 24%) of compound 1. The thus prepared compound 1 was found to be a mixture of oxime-based isomers (about 4:1) according to $^1$H—NMR.
FAB-MS m/z: 505 [M+E]$^+$
Major component: $^1$H—NMR (CD$_3$OD) δ(ppm): 7.27 (1H, dd, 15.8, 10.9 Hz), 6.80 (1H, d, 16.3 Hz), 6.44 (1H, s), 6.17 (1H, dd, 11.9, 10.9 Hz), 5.61 (1H, dd, 10.9, 3.5 Hz), 5.31 (1H, m), 4.80 (2H, s), 3.93 (1H, d, 15.9 Hz), 3.82 (1H, d, 16.3 Hz), 3.40–3.60 (4H, m), 3.34 (1H, m), 3.02 (1H, m), 2.49 (1H, ddd, 14.4, 3.5, 3.5 Hz), 1.60–1.80 (7H, m), 1.52 (3H, d, 6.4 Hz).

EXAMPLE 2

Compound 2:

According to (1-2) described in Example 1, 109 mg (yield, 49%) of compound 2 was prepared from 200 mg (0.457 mmol) of compound (K), 77 mg (0.503 mmol) of HOBt, 96 mg (0.503 mmol) of EDCI and 0.042 ml (0.503 mmol) of pyrroridine. The thus prepared compound 2 was found to be a mixture of oxime-based isomers (about 3:1) according to $^1$H—NMR.
FAB-MS m/z: 491 [M+H]$^+$
Major component: $^1$H—NMR (DMSO-d$_6$) δ(ppm): 10.34 (1H, br s), 10.00 (1H, br s), 7.14 (1H, dd, 16.0, 11.4 Hz), 6,74 (1H, d, 15.8 Hz), 6.51 (1H, s), 6.23 (1H, dd, 11.2, 10.9 Hz), 5.63 (1H, dd, 10.4, 3.5 Hz), 5.14 (1H, m), 4.68 (2H, s), 3.80 (1H, d, 15.8 Hz), 3.51 (1H, d, 15.2 Hz), 3.27–3.54 (4H, m), 3.05 (1H, m), 2.44 (1H, m), 1.70–1.91 (5H, m), 1.43 (3H, d, 6.3 Hz).

EXAMPLE 3

Compound 3:

According to (1-2) described in Example 1, 42 mg (yield, 12%) of compound 3 was prepared from 300 mg (0.685 mmol) of compound (K), 155 mg (0.753 mmol) of DCC, 87 mg (0.753 mmol) of HONSu and 0.090 ml (0.753 mmol) of morpholine. The thus prepared compound 3 was found to be a mixture of oxime-based isomers (about 4:1) according to $^1$H—NMR.
FAB-MS m/z: 507 [M+H]$^+$
Major component: $^1$H—NMR (CD$_3$OD) δ(ppm): 7.28 (1H, dd, 15.8, 11.4 Hz), 6.78 (1H, d, 16.3 Hz), 6.42 (1H, s), 6.17 (1H, dd, 11.4, 10.4 Hz), 5.62 (1H, dd, 10.4, 3.0 Hz), 5.30 (1H, m), 4.82 (2H, s), 3.87 (1H, d, 15.8 Hz), 3.82 (1H, d, 16.3 Hz), 3.57–3.71 (8H, m), 3.34 (1H, m), 3.05 (1H, m), 2.42 (1H, ddd, 14.4, 4.0, 3.5 Hz), 1.94 (1H, m), 1.52 (3H, d, 6.9 Hz).

EXAMPLE 4

Compound 4:

According to (1-2) described in Example 1, 24 mg (yield, 20%) of compound 4 was prepared from 100 mg (0.288 mmol) of compound (K), 52 mg (0.251 mmol) of DCC, 29 mg (0.251 mmol) of HONSu and 0.028 ml (0.251 mmol) of 1-methylpiperazine. The thus prepared compound 4 was found to be a mixture of oxime-based isomers (about 4:1) according to $^1$H—NMR.
FAB-MS m/z: 520 [M+H]$^+$
Major component: $^1$H—NMR (CD$_3$OD) δ(ppm): 7.01 (1H, dd, 15.8, 11.4 Hz), 6.69 (1H, d, 15.8 Hz), 6.33 (1H, s), 6.07 (1H, t, 10.9 Hz), 5.52 (1H, dd, 10.4, 4.0 Hz), 5.20 (1H, m), 4.72 (2H, s), 3.84 (1H, d, 16.3 Hz), 3.72 (1H, d, 16.3 Hz), 3.41–3.55 (4H, m), 3.25 (1H, m), 2.92 (1H, m), 2.28–2.41 (5H, m), 2.22 (3H, s), 1.50 (1H, m), 1.42 (3H, d, 6.4 Hz).

EXAMPLE 5

Compound 5:

According to (1-2) described in Example 1, 46 mg (yield, 37%) of compound 5 was prepared from 100 mg (0.288 mmol) of compound (K), 52 mg (0.251 mmol) of DCC, 29 mg (0.251 mmol) of HONSu and 0.035 ml (0.251 mmol) of N,N-diethylethylenediamine. The thus prepared compound 5 was found to be a mixture of oxime-based isomers (about 3:1) according to $^1$H—NMR.
FAB-MS m/z: 537 [M+H]$^+$
Major component: 1H—NMR (CD$_3$OD) δ(ppm): 7.30 (1H, dd, 15.8, 11.4 Hz), 6.84 (1H, d, 16.3 Hz), 6.39 (1H, s), 6.18 (1H, t, 10.9 Hz), 5.63 (1H, dd, 10.9, 3.5 Hz), 5.30 (1H, m), 3.96 (2H, br), 3.44–3.52 (2H, m), 3.36 (1H, m), 3.00 (1H, m), 2.77–2.82 (6H, m), 2.60 (1H, m), 1.67 (1H, m), 1.51 (3H, d, 6.4 Hz), 1.07–1.19 (6H, m).

EXAMPLE 6

Compound 6:

According to (1-2) described in Example 1, 87 mg (yield, 40%) of compound 6 was prepared from 200 mg (0.456 mmol) of compound (K), 88 mg (0.457 mmol) of EDCI, 56 mg (0.457 mmol) of DMAP and 25 mg (0.457 mmol) of 2-aminoethanol. The thus prepared compound 6 was found to be a mixture of oxime-based isomers (about 5:1) according to $^1$H—NMR.
Major component: $^1$H—NMR (CD$_3$OD) δ(ppm): 7.30 (1H, dd, 15.8, 11.4 Hz), 6.85 (1H, d, 16.3 Hz), 6.44 (1H, s), 6.19 (1H, t, 10.9 Hz), 5.63 (1H, dd, 10.9, 3.0 Hz), 5.31 (1H, m), 4.58 (2H, s), 3.96 (1H, d, 16.3 Hz), 3.85 (1H, d, 16.3 Hz), 3.54–3.70 (2H, m), 3.31–3.40 (2H, m), 3.31 (1H, m), 3.02 (1H, m), 2.43 (1H, m), 1.61 (1H, m), 1.52 (3H, d, 6.4 Hz).

EXAMPLE 7

Compound 7:

According to (1-2) described in Example 1, 45 mg (yield, 13%) of compound 7 was prepared from 300 mg (0.685 mmol) of compound (K), 132 mg (0.685 mmol) of EDCI, 84 mg (0.685 mmol) of DMAP and 97 mg (0.685 mmol) of 2,2'-iminodiethanol hydrochloride. The thus prepared compound 7 was found to be a mixture of oxime-based isomers (about 5:1) according to $^1$H—NMR.

Major component: $^1$H—NMR (CD$_3$OD) δ(ppm): 7.26 (1H, dd, 15.8, 10.9 Hz), 6.83 (1H, d, 15.8 Hz), 6.42 (1H, s), 6.17 (1H, dd, 11.4, 10.4 Hz), 5.60 (1H, dd, 10.4, 3.5 Hz), 5.29 (1H, m), 4.91 (2H, s), 3.91 (1H, d, 15.8 Hz), 3.80 (1H, d, 15.8 Hz), 3.71–3.90 (4H, m), 3.52–3.59 (4H, m), 3.34 (1H, m), 3.00 (1H, m), 2.42 (1H, ddd, 14.8, 3.5, 3.5 Hz), 1.60 (1H, m), 1.52 (3H, d, 6.4 Hz).

EXAMPLE 8

Compound 8:

According to (1-2) described in Example 1, 89 mg (yield, 38%) of compound 8 was prepared from 200 mg (0.456 mmol) of compound (K), 87 mg (0.456 mmol) of EDCI, 56 mg (0.457 mmol) of DMAP and 63 mg (0.502 mmol) of glycine methyl ester hydrochloride. The thus prepared compound 8 was found to be a mixture of oxime-based isomers (about 4:1) according to $^1$H—NMR.

FAB-MS m/z: 509 [M+H]$^+$

Major component: $^1$H—NMR (CD$_3$OD) δ(ppm): 7.30 (1H, dd, 16.3, 11.9 Hz), 6.87 (1H, d, 15.8 Hz), 6.44 (1H, s), 6.20 (1H, dd, 10.4, 9.4 Hz), 5.63 (1H, dd, 10.4, 4.0 Hz), 5.31 (1H, m), 4.85 (2H, s), 4.02 (1H, d, 2.0 Hz), 3.96 (1H, d, 15.8 Hz), 3.83 (1H, d, 15.8 Hz), 3.73 (3H, s), 3.36 (1H, m), 3.03 (1H, m), 2.44 (1H, ddd, 14.3, 3.5, 3.5 Hz), 1.65 (1H, m), 1.53 (3H, d, 6.4 Hz).

EXAMPLE 9

Compound 9:

A 46 mg (0.150 mmol) portion of compound (K) was dissolved in 1.5 ml of tetrahydrofuran, and the solution was mixed with 23 mg (0.200 mmol) of HOBt, 2.7 mg (0.022 mmol) of DMAP and 44 mg (0.228 mmol) of EDCI and stirred at room temperature for 16 hours. The resulting precipitate was separated by filtration, and the solvent was evaporated under reduced pressure. The thus prepared residue was dissolved in 1.5 ml of tetrahydrofuran, and the solution was mixed with 0.100 ml (0.720 mmol) of triethylamine and 0.050 ml (1.030 mmol) of hydrazine hydrate and stirred at room temperature for 12 hours. The reaction solution was mixed with ethyl acetate, washed with a saturated ammonium chloride aqueous solution and dried with anhydrous sodium sulfate, and then the solvent was evaporated under reduced pressure. The resulting residue was purified by silica gel column chromatography (chloroform/methanol=24/1) to obtain 33 mg (yield, 48%) of compound 9. The thus prepared compound 9 was found to be a mixture of oxime-based isomers (about 3:1) according to $^1$H—NMR.

FAB-MS m/z: 452 [M+H]$^+$

Major component: $^1$H—NMR (CD$_3$OD) δ(ppm): 7.28 (1H, dd, 16.1, 11.3 Hz), 6.83 (1H, d, 16.1 Hz), 6.43 (1H, s), 6.19 (1H, dd, 11.3, 10.7 Hz), 5.62 (1H, dd, 10.7, 3.7 Hz), 5.30 (1H, m), 3.94 (1H, d, 16.1 Hz), 3.79 (1H, d, 16.1 Hz), 3.31 (1H, m), 3.02 (1H, m), 2.43 (1H, m), 1.59 (1H, m), 1.52 (3H, d, 6.5 Hz).

EXAMPLE 10

Compound 10:

According to (1-2) described in Example 1, 35 mg (yield, 27%) of compound 10 was prepared from 100 mg (0.228 mmol) of compound (K), 44 mg (0.228 mmol) of EDCI and 35 mg (0.228 mmol) of 4-phenylsemicarbazide. The thus prepared compound 10 was found to be a mixture of oxime-based isomers (about 5:1) according to $^1$H—NMR.

Major component: $^1$H—NMR (CD$_3$OD) δ(ppm): 7.23–7.42 (5H, m), 7.02 (1H, t, 7.4 Hz), 6.88 (1H, d, 15.8 Hz), 6.45 (1H, s), 6.18 (1H, t, 10.9 Hz), 5.62 (1H, dd, 10.9, 3.5 Hz), 5.31 (1H, m), 4.73 (2H, s), 3.97 (1H, d, 16.3 Hz), 3.86 (1H, d, 16.3 Hz), 3.36 (1H, m), 3.01 (1H, m), 2.42 (1H, ddd, 14.3, 3.5, 3.5 Hz), 1.61 (1H, m), 1.51 (3H, d, 6.4 Hz).

EXAMPLES 11–37

Compounds 11 to 38 were prepared from compound (K) according to (1-2) described in Example 1.

EXAMPLE 11

Compound 11:

Isomer ratio: about 10:1

FAB-MS m/z: 519 [M+H]$^+$

Major component: $^1$H—NMR (CDCl$_3$) δ(ppm): 10.78 (1H, br), 7.86 (1H, br s), 7.14 (1H, dd, 15.8, 11.6 Hz), 6.75 (1H, d, 15.8 Hz), 6.60 (1H, s), 6.09 (1H, dd, 11.6, 10.2 Hz), 5.60 (1H, dd, 10.6, 3.0 Hz), 5.47 (1H, m), 4.85 (1H, d, 13.9 Hz), 4.79 (1H, d, 13.9 Hz), 4.69 (1H, br), 3.98 (1H, br), 3.37–3.56 (4H, m), 3.16 (1H, br), 2.94 (2H, dd, 8.6, 2.6, 2.3 Hz), 2.31 (1H, ddd, 15.2, 3.6, 3.6 Hz), 1.95 (1H, ddd, 15.2, 8.9, 4.0 Hz), 1.74 (2H, br), 1.53 (3H, d, 6.9 Hz), 1.49–1.58 (2H, br), 1.20–1.29 (4H, br).

EXAMPLE 12

Compound 12:

Isomer ratio: about 3:1

FAB-MS m/z: 519 [M+H]$^+$

Major component: $^1$H—NMR (CDCl$_3$) δ(ppm): 10.99 (1H, br), 8.00 (1H, br), 7.16 (1H, m), 6.73 (1H, d, 16.2 Hz), 6.59 (1H, s), 6.11 (1H, dd, 10.6, 10.2 Hz), 5.62 (1H, br d, 9.6 Hz), 5.48 (1H, m), 4.80 (2H, s), 4.67 (1H, d, 12.2 Hz), 4.54 (2H, br), 4.00 (1H, br), 3.73–3.89 (2H, br), 3.17 (1H, br), 3.04 (1H, m), 2.50–2.65 (2H, m), 2.32 (1H, ddd, 15.2, 3.6, 3.3 Hz), 1.93 (1H, ddd, 18.8, 9.2, 4.6 Hz), 1.58–1.70 (2H, m), 1.54 (3H, d, 6.9 Hz), 1.04–1.19 (2H, m), 0.94 (3H, d, 6.3 Hz).

EXAMPLE 13

Compound 13:

Isomer ratio: about 3:1

FAB-MS m/z: 521 [M+H]$^+$

Major component: $^1$H—NMR (CDCl$_3$) δ(ppm): 7.16 (1H, m), 6.70 (1H, d, 16.2 Hz), 6.57 (1H, s), 6.11 (1H, dd, 10.6, 10.2 Hz), 5.63 (1H, br d, 11.2 Hz), 5.48 (1H, m), 4.80 (2H, s), 4.63 (1H, br), 3.95 (3H, br), 3.76 (1H, br), 3.19–3.47 (3H, m), 2.96 (1H, br), 2.33 (1H, m), 1.90 (1H, m), 1.54 (3H, d, 6.6 Hz), 1.20–1.28 (4H, m).

EXAMPLE 14

Compound 14:

Isomer ratio: about 8:1

FAB-MS m/z: 588 [M+H]$^+$

Major component: $^1$H—NMR (CDCl$_3$+CD$_3$OD) δ(ppm): 7.01 (1H, dd, 16.0, 11.0 Hz), 6.62 (1H, d, 15.8 Hz), 6.34 (1H, s), 6.06 (1H, dd, 11.6, 9.9 Hz), 5.46 (1H, br d, 10.6 Hz), 5.34 (1H, br), 4.68 (2H, s), 4.55 (1H, d, 17.8 Hz), 3.96 (1H, br), 3.20 (1H, br), 2.82–2.99 (2H, m), 2.60 (8H, br), 2.25 (1H, br d, 11.6 Hz), 1.89 (2H, br), 1.70–1.80 (4H, br), 1.61 (4H, br), 1.44 (3H, d, 6.6 Hz).

EXAMPLE 15

Compound 15:
Isomer ratio: about 3:1
FAB-MS m/z: 548 [M+H]$^+$
Major component: $^1$H—NMR (CDCl$_3$) δ(ppm): 7.13 (1H, dd, 16.0, 11.4 Hz), 6.64 (1H, d, 16.2 Hz), 6.41 (1H, s), 6.06 (1, dd, 11.9, 10.2 Hz), 5.57 (1H, dd, 10.2, 3.0 Hz), 5.37 (1H, m), 4.70 (2H, s), 4.33–4.52 (2H, m), 3.91–4.01 (2H, m), 3.17 (1H, br), 2.80–3.08 (2H, m), 2.66 (1H, m), 2.24–2.40 (2H, m), 1.54–1.84 (5H, br), 1.47 (3H, d, 6.6 Hz).

EXAMPLE 16

Compound 16:
Isomer ratio: about 4:1
FAB-MS m/z: 577 [M+H]$^+$
Major component: $^1$H—NMR (CDCl$_3$) δ(ppm): 10.71 (1H, br) 8.83 (1H, br), 7.23 (1H, dd, 16.0, 11.4 Hz), 6.66 (1H, d, 16.2 Hz), 6.60 (1H, s), 6.41 (1H, t, 5.8 Hz), 6.13 (1H, dd, 11.2, 10.9 Hz), 5.67 (1H, dd, 10.2, 3.0 Hz), 5.47 (1H, m), 4.66 (1H, br), 4.59 (2H, s), 4.02 (1H, d, 15.2 Hz), 3.25–3.35 (2H, m), 3.20 (1H, br), 2.95 (1H, m), 2.33 (1H, m), 1.95 (1H, m), 1.54 (3H, d, 6.6 Hz), 1.51 (2H, br), 1.21 (14H, br), 0.83 (3H, t, 5.6 Hz).

EXAMPLE 17

Compound 17:
Isomer ratio: about 13:1
FAB-MS m/z: 513 [M+H]$^+$
Major component: $^1$H—NMR (CDCl$_3$) δ(ppm): 10.77 (1H, br), 7.25 (1H, dd, 16.2, 11.2 Hz), 7.02 (1H, br), 6.68 (1H, d, 16.2 Hz), 6.61 (1H, s), 6.51 (1H, t, 5.9 Hz), 6.17 (1H, dd. 11.2, 10.6 Hz), 5.71 (1H, dd, 10.2, 3.3 Hz), 5.51 (1H, m), 4.73 (1H, d, 15.8 Hz), 4.62 (2H, s), 4.06 (1H, d, 15.2 Hz), 3.61 (2H, t, 6.3 Hz), 3.45–3.54 (2H, m), 3.22 (1H, br), 2.99 (1H, ddd, 8.3, 2.6, 2.6 Hz), 2.36 (1H, ddd, 15.2, 3.6, 3.6 Hz), 1.95–2.10 (3H, m), 1.58 (3H, d, 6.6 Hz).

EXAMPLE 18

Compound 18:
Isomer ratio: about 10:1
FAB-MS m/z: 509 [M+H]$^+$
Major component: $^1$H—NMR (CDCl$_3$) δ(ppm): 10.76 (1H, br), 7.23 (1H, dd, 15.5, 10.9 Hz), 6.84 (1H, br), 6.69 (1H, d, 16.2 Hz), 6.67 (1H, br), 6.16 (1H, dd, 11.2, 10.6 Hz), 5.70 (1H, dd, 10.4, 3.1 Hz), 5.51 (1H, m), 4.75 (1H, br), 4.64 (2H, s), 4.10 (1H, br), 3.45–3.57 (6H, m), 3.22 (1H, br), 2.99 (1H, ddd, 8.3, 2.6, 2.3 Hz), 2.36 (1H, ddd, 15.2, 3.6, 3.3 Hz), 2.00 (1H, ddd, 15.2, 8.6, 4.0 Hz), 1.58 (3H, d, 6.6 Hz), 1.14 (3H, t, 7.1 Hz).

EXAMPLE 19

Compound 19:
Isomer ratio: about 3:1
FAB-MS m/z: 477 [M+H]$^+$
Major component: $^1$H—NMR (CDCl$_3$) δ(ppm): 10.77 (1H, br), 7.47 (1H, br), 7.24 (1H, dd, 16.1, 11.2 Hz), 6.68 (1H, d, 16.2 Hz), 6.61 (1H, s), 6.40 (1H, br), 6.16 (1H, dd, 11.6, 11.5 Hz), 5.86 (1H, m), 5.70 (1H, dd, 10.2, 3.3 Hz), 5.51 (1H, m), 5.23 (1H, dd, 17.2, 1.3 Hz), 5.16 (1H, dd, 10.2, 1.3 Hz), 4.71 (1H, br), 4.64 (2H, s), 3.96–3.98 (3H, m), 3.21 (1H, br), 2.99 (1H, m), 2.35 (1H, ddd, 15.2, 3.6, 3.3 Hz), 1.98 (1H, ddd, 15.2, 8.9, 4.0 Hz), 1.56 (3H, d, 6.9 Hz).

EXAMPLE 20

Compound 20:
Isomer ratio: about 4:1
FAB-MS m/z: 533 [M+H]$^+$
Major component: $^1$H—NMR (CDCl$_3$) δ(ppm): 10.75 (1H, br), 8.17 (1H, br), 7.24 (1H, dd, 16.2, 11.2 Hz), 6.68 (1H, d, 15.8 Hz), 6.42 (1H, t, 6.1 Hz), 6.16 (1H, dd. 11.2, 10.6 Hz), 5.69 (1H, dd, 10.4, 3.1 Hz), 5.50 (1H, m), 4.61 (2H, s), 4.04 (1H, d, 14.2 Hz), 3.09–3.27 (4H, m), 2.99 (1H, m), 2.35 (1H, ddd, 15.2, 3.3, 3.3 Hz), 1.98 (1H, m), 1.68–1.73 (6H, br), 1.56 (3H, d, 6.6 Hz), 1.49 (1H, br), 1.10–1.24 (4H, br).

EXAMPLE 21

Compound 21:
Isomer ratio: about 7:1
FAB-MS m/z: 617 [M+H]$^+$
Major component: $^1$H—NMR (CDCl$_3$) δ(ppm): 10.71 (1H, br), 7.75 (1H, br), 7.20 (1H, dd, 16.0, 11.4 Hz), 6.64 (1H, d, 15.8 Hz), 6.54 (1H, s), 6.52–6.64 (3H, m), 6.11 (1H, dd, 11.5, 10.2 Hz), 5.67 (1H, dd, 10.2, 3.3 Hz), 5.46 (1H, m), 4.69 (1H, d, 13.5 Hz), 4.63 (1H, d, 16.2 Hz), 4.62 (1H, br), 4.45 (1H, d, 5.9 Hz), 3.99 (1H, d, 15.8 Hz), 3.83 (3H, s), 3.82 (3H, s), 3.81 (3H, s), 3.18 (1H, br), 2.96 (1H, m), 2.33 (1H, ddd, 15.2, 3.6, 3.6 Hz), 1.95 (1H, ddd, 15.2, 8.6, 3.9 Hz), 1.52 (3H, d, 6.6 Hz).

EXAMPLE 22

Compound 22:
Isomer ratio: about 3:1
FAB-MS m/z: 528 [M+H]$^+$
Major component: $^1$H—NMR (CDCl$_3$) δ(ppm): 8.57 (1H, br s), 8.47 (1H, br d, 4.3 Hz), 7.81 (1H, ddd, 8.2, 2.0, 1.7 Hz), 7.36 (1H, dd, 7.9, 4.6 Hz), 7.20 (1H, dd, 15.8, 11.2 Hz), 6.93 (1H, t, 6.3 Hz), 6.65 (1H, d, 16.2 Hz), 6.46 (1H, s), 6.10 (1H, dd, 10.6, 9.9 Hz), 5.67 (1H, dd, 10.2, 3.0 Hz), 5.45 (1H, m), 4.48–4.64 (5H, m), 3.90 (1H, d, 15.2 Hz), 3.15 (1H, br), 2.94 (1H, br d, 8.9 Hz), 2.31 (1H, ddd, 15.2, 3.3, 3.3 Hz), 1.92 (1H, m), 1.52 (3H, d, 6.9 Hz).

EXAMPLE 23

Compound 23:
Isomer ratio: about 3:1
FAB-MS m/z: 544 [M+H]$^+$
Major component: $^1$H—NMR (CDCl$_3$) δ(ppm): 10.70 (1H, br), 9.02 (1H, br), 7.22 (1H, dd, 15.8, 11.2 Hz), 6.61–6.65 (2H, m), 6.60 (1H, s), 6.53 (1H, m), 6.15 (1H, dd, 10.9, 10.6 Hz), 5.89–5.98 (2H, m), 5.68 (1H, dd, 10.2, 3.0 Hz), 5.47 (1H, m), 4.64 (1H, d, 15.5 Hz), 4.61 (1H, br), 4.58 (1H, d, 16.2 Hz), 4.06 (1H, br), 3.41–3.60 (2H, m), 3.54 (3H, s), 3.23 (1H, br), 3.00 (1H, m), 2.81 (2H, m), 2.34 (1H, ddd, 15.2, 3.3, 3.3 Hz), 1.96 (1H, ddd, 16.2, 8.9, 4.0 Hz), 1.55 (3H, d, 6.6 Hz).

EXAMPLE 24

Compounds 24 and 25:
Compound 24:
FAB-MS m/z: 548 [M+H]$^+$
$^1$H—NMR (CDCl$_3$) δ(ppm): 7.61 (1H, br), 7.16 (1H, dd, 16.0, 11.4 Hz), 6.85 (2H, br), 6.60 (1H, d, 16.2 Hz), 6.45 (1H, s), 5.79 (1H, dd, 11.2, 10.9 Hz), 5.57 (1H, dd, 10.2, 3.0 Hz), 5.43 (1H, m), 4.70 (1H, br), 4.67 (1H, d, 15.8 Hz), 4.59 (1H, d, 15.8 Hz), 3.95 (1H, br), 3.51–3.72 (2H, m), 3.15 (1H, br), 2.93 (1H, br d, 8.6 Hz), 2.80 (2H, t, 5.6 Hz), 2.72 (4H, br), 2.30 (1H, ddd, 14.9, 3.3, 3.3 Hz), 1.98 (1H, ddd, 14.9, 8.9, 4.0 Hz), 1.52 (3H, d, 6.6 Hz), 1.45–1.63 (6H, br).
Compound 25:
FAB-MS m/z: 548 [M+H]$^+$
$^1$H—NMR (CDCl$_3$) δ(ppm): 8.58 (1H, br), 7.05 (1H, dd, 16.2, 11.2 Hz), 6.29 (1H, s), 5.98 (1H, d, 16.2 Hz), 5.98 (1H, dd, 10.9, 9.2 Hz), 5.55 (1H, br d, 10.2 Hz), 5.45 (1H, m), 4.78 (1H, d, 15.8 Hz), 4.68 (1H, d, 15.5 Hz), 4.07 (2H, br), 3.98 (1H, br), 3.69 (1H, br), 2.84–3.04 (8H, m), 2.22 (1H, br d, 14.9 Hz), 2.04 (1H, ddd, 14.5, 10.4, 4.3 Hz), 1.54 (3H, d, 6.9 Hz), 1.20–1.48 (6H, br), 1.57 (3H, d, 6.9 Hz).

EXAMPLE 25

Compound 26:
Isomer ratio: about 3:1
FAB-MS m/z: 562 [M+H]$^+$
Major component: $^1$H—NMR (CDCl$_3$) δ(ppm): 10.92 (1H, br), 9.00 (1H, br), 7.17 (1H, m), 7.05 (1H, m), 6.81 (1H, d, 15.8 Hz), 6.56 (1H, s), 6.16 (1H, t, 10.6 Hz), 5.63 (1H, dd, 10.4, 3.1 Hz), 5.44 (1H, m), 4.64 (1H, d, 19.5 Hz), 4.60 (1H, br), 4.57 (1H, d, 17.8 Hz), 4.06 (1H, br), 3.40 (2H, t, 6.9 Hz), 3.25–3.36 (4H, m), 3.21 (1H, br), 2.96 (1H, br d, 8.2 Hz), 2.30–2.42 (3H, m), 2.03 (2H, t, 7.6 Hz), 2.00 (1H, m), 1.77 (2H, m), 1.54 (3H, d, 6.6 Hz).

EXAMPLE 26

Compound 27:
Isomer ratio: about 3:1
FAB-MS m/z: 505 [M+H]$^+$
Major component: $^1$H—NMR (CDCl$_3$) δ(ppm): 10.75 (1H, br), 8.50 (1H, br), 7.23 (1H, dd, 16.0, 11.4 Hz), 6.67 (1H, d, 16.2 Hz), 6.61 (1H, s), 6.32 (1H, d, 7.6 Hz), 6.14 (1H, dd, 11.9, 10.2 Hz), 5.68 (1H, dd, 10.4, 3.1 Hz), 5.49 (1, m), 4.67 (1H, d, 15.8 Hz), 4.58 (2H, s), 4.26 (1H, m), 3.99 (1H, d, 15.8 Hz), 3.19 (1H, br), 2.96 (1H, m), 2.33 (1H, ddd, 15.2, 3.3, 3.3 Hz), 1.89–2.04 (3H, m), 1.58–1.66 (4H, m), 1.55 (3H, d, 6.6 Hz), 1.38–1.43 (2H, m).

EXAMPLE 27

Compound 28:
Isomer ratio: about 3:1
FAB-MS m/z: 513 [M+H]$^+$
Major component: $^1$H—NMR (CDCl$_3$) δ(ppm): 10.76 (1H, br), 7.48–7.56 (2H, m), 7.25–7.37 (3H, m), 7.07–7.16 (2H, m), 6.77 (1H, d, 16.2 Hz), 6.61 (1H, s), 6.21 (1H, dd, 11.6, 10.6 Hz), 5.74 (1H, dd, 10.2, 3.6 Hz), 5.52 (1H, m), 4.80 (1H, br), 4.73 (2H, s), 4.12 (1H, br), 3.23 (1H, br), 2.99 (1H, ddd, 8.3, 3.3, 2.6 Hz), 2.36 (1H, ddd, 15.2, 3.6, 3.3 Hz), 1.99 (1H, ddd, 15.2, 8.6, 4.0 Hz), 1.57 (3H, d, 6.9 Hz).

EXAMPLE 28

Compound 29:
Isomer ratio: about 4:1
FAB-MS m/z: 555 [M+H]$^+$
Major component: $^1$H—NMR (CDCl$_3$) δ(ppm): 8.00 (1H, br s), 7.43 (2H, d, 8.6 Hz), 7.19 (2H, d, 8.3 Hz), 7.20 (1H, m), 6.77 (1H, d, 16.2 Hz), 6.59 (1H, s), 6.19 (1H, dd, 10.6, 9.9 Hz), 5.73 (1H, dd, 10.2, 3.3 Hz), 5.49 (1H, m), 4.72 (2H, s), 4.72 (1H, br), 4.09 (1H, br), 3.22 (1H, br), 2.82–3.01 (2H, m), 2.35 (1H, dd, 15.2, 3.3, 3.3 Hz), 1.98 (1H, ddd, 15.2, 8.6, 4.0 Hz), 1.55 (3H, d, 6.6 Hz), 1.22 (6H, d, 6.9 Hz).

EXAMPLE 29

Compound 30:
Isomer ratio: about 3:1
FAB-MS m/z: 543 [M+H]$^+$
Major component: $^1$H—NMR (CDCl$_3$) δ(ppm): 7.97 (1H, d, 9.2 Hz), 7.38–7.44 (2H, m), 7.26 (1H, dd, 15.8, 11.5 Hz), 6.81–6.86 (2H, m), 6.75 (1H, d, 16.2 Hz), 6.56 (1H, s), 6.16 (1H, dd, 11.6, 10.2 Hz), 5.69 (1H, dd, 10.6, 3.3 Hz), 5.47 (1H, m), 4.73 (1H, d, 16.5 Hz), 4.67 (1H, d, 14.9 Hz), 4.64 (1H, br), 4.04 (1H, d, 14.5 Hz), 3.75 (3H, s), 3.20 (1H, br), 2.96 (1H, ddd, 9.9, 3.6, 2.3 Hz), 2.33 (1H, ddd, 15.2, 3.6, 3.3 Hz), 1.94 (1H, ddd, 15.2, 8.9, 4.0 Hz), 1.53 (3H, d, 6.9 Hz).

EXAMPLE 30

Compound 31:
Isomer ratio: about 3:1
FAB-MS m/z: 584 [M+H]$^+$
Major component: $^1$H—NMR (CDCl$_3$) δ(ppm): 7.98 (1H, br s), 7.32 (2H, d, 8.9 Hz), 7.29 (1H, m), 6.75 (1H, d, 16.2 Hz), 6.64 (2H, d, 8.9 Hz), 6.58 (1H, s), 6.18 (1H, dd, 11.9, 9.9 Hz), 5.71 (1H, dd, 10.2, 3.0 Hz), 5.48 (1H, m), 4.72 (1H, d, 16.8 Hz), 4.71 (2H, s), 4.04 (1H, d, 15.8 Hz), 3.31 (4H, q, 7.1 Hz), 3.21 (1H, br), 2.99 (1H, ddd, 8.6, 2.6, 2.3 Hz), 2.34 (1H, ddd, 15.2, 3.6, 3.3 Hz), 1.96 (1H, ddd, 15.2, 8.6, 4.0 Hz), 1.55 (3H, d, 6.6 Hz), 1.12 (6H, t, 7.1 Hz).

EXAMPLE 31

Compound 32:
Isomer ratio: about 3:1
FAB-MS m/z: 514 [M+H]$^+$
Major component: $^1$H—NMR (CDCl$_3$) δ(ppm): 8.56 (1H, br d, 7.9 Hz), 8.46 (1H, m), 8.30–8.34 (2H, m), 7.31–7.42 (2H, m), 6.76 (1H, d, 16.2 Hz), 6.52 (1H, s), 6.17 (1H, dd, 10.9, 9.9 Hz), 5.72 (1H, dd, 10.2, 3.0 Hz), 5.48 (1H, m), 4.80 (1H, br), 4.77 (1H, d, 16.5 Hz), 4.70 (1H, d, 16.5 Hz), 4.03 (1H, d, 16.5 Hz), 3.20 (1H, br), 2.95 (1H, m), 2.34 (1H, ddd, 15.2, 3.3, 3.3 Hz), 1.97 (1H, ddd, 15.2, 8.9, 4.0 Hz), 1.56 (3H, d, 6.9 Hz)

EXAMPLE 32

Compound 33:
Isomer ratio: about 3:1
FAB-MS m/z: 480 [M+H]$^+$
Major component: $^1$H—NMR (CDCl$_3$) δ(ppm): 10.77 (1H, br s), 7.24 (1H, dd, 16.2, 11.2 Hz), 7.00 (1H, br s), 6.67 (1H, d, 16.5 Hz), 6.64 (1H, s), 6.17 (1H, dd, 11.2, 10.6 Hz), 5.71 (1H, dd, 10.2, 3.0 Hz), 5.53 (1H, m), 4.75 (1H, br), 4.62 (2H, s), 4.08 (1H, br), 3.22 (1H, br), 2.99 (1H, br d, 8.3 Hz), 2.63 (6H, s), 2.36 (1H, ddd, 14.8, 3.6, 3.6 Hz), 1.99 (1H, ddd, 15.5, 8.6, 4.1 Hz), 1.57 (3H, d, 6.6 Hz).

EXAMPLE 33

Compound 34:
Isomer ratio: about 3:1
FAB-MS m/z: 496 [M+H]$^+$
Major component: $^1$H—NMR (CDCl$_3$) δ(ppm): 10.70 (1H, br), 7.72 (1H, br), 7.24 (1H, dd, 15.2, 11.5 Hz), 6.66 (1H, d, 16.2 Hz), 6.60 (1H, s), 6.17 (1H, dd, 11.9, 10.2 Hz), 5.72 (1H, dd, 10.4, 3.5 Hz), 5.51 (1H, m), 4.70 (1H, br), 4.70 (2H, s), 4.10 (1H, br), 3.62 (2H, t, 4.6 Hz), 2.96–2.98 (3H, m), 2.36 (1H, ddd, 15.5, 3.8, 3.3 Hz), 2.00 (1H, ddd, 15.5, 8.6, 4.0 Hz), 1.58 (3H, d, 6.9 Hz).

EXAMPLE 34

Compound 35:
Isomer ratio: about 3:1
FAB-MS m/z: 528 [M+H]$^+$
Major component: $^1$H—NMR (CDCl$_3$) δ(ppm): 10.75 (1S, br), 8.01 (1S, br s), 7.19–7.25 (2H, m), 7.00 (1H, dd, 15.2, 10.9 Hz), 6.86–6.93 (4H, m), 6.71 (1H, d, 16.2 Hz), 6.58 (1H, s), 6.18 (1H, dd, 10.6, 9.9 Hz), 5.72 (1H, dd, 10.4, 3.1 Hz), 5.50 (1H, m), 4.82 (1H, br), 4.76 (2H, s), 4.12 (1S, d, 14.2 Hz), 3.22 (1H, br), 2.97 (1H, m), 2.35 (1H, ddd, 15.2, 3.6, 3.3 Hz), 1.99 (1H, ddd, 15.2, 8.6, 4.3 Hz), 1.55 (3H, d, 6.6 Hz).

EXAMPLE 35

Compound 36:
Isomer ratio: about 4:1
FAB-MS m/z: 529 [M+H]$^+$
Major component: $^1$H—NMR (CDCl$_3$) δ(ppm): 8.30 (1H, br), 8.10 (1H, br d, 4.6 Hz), 8.07 (1H, br), 7.52 (1H, dd, 7.6, 6.6 Hz), 7.22 (1S, m), 6.67–6.87 (3S, m), 6.54 (1H, s), 6.15 (1H, dd, 11.2, 10.9 Hz), 5.70 (1H, dd, 10.2, 3.0 Hz), 5.48 (1H, m), 4.74 (2H, s), 4.67 (1H, d, 15.5 Hz), 4.08 (1H, br), 3.23 (1H, br), 2.98 (1H, br d, 8.3 Hz), 2.35 (1H, br d, 15.5 Hz), 1.98 (1H, m), 1.55 (3H, d, 6.6 Hz).

EXAMPLE 36

Compound 37:
Isomer ratio: about 2:1
FAB-MS m/z: 520 [M+H]$^+$
Major component: $^1$H—NMR (CDCl$_3$) δ(ppm): 10.80 (1H, br), 8.50 (1H, br), 7.25 (1H, dd, 15.8, 11.2 Hz), 7.06 (1H, s), 6.67 (1H, d, 13.5 Hz), 6.64 (1H, s), 6.16 (1H, dd, 11.2, 10.9 Hz), 5.70 (1H, dd, 10.2, 3.0 Hz), 5.50 (1H, m), 4.69 (1H, d, 15.8 Hz) 4.62 (2H, s), 4.01 (1H, d, 14.9 Hz), 3.19 (1H, br), 2.96 (1H, m), 2.73 (4H, br), 2.34 (1H, ddd, 15.2, 3.6, 3.0 Hz), 1.96 (1H, ddd, 15.2, 8.4, 4.1 Hz), 1.66 (6H, br), 1.56 (3H, d, 6.9 Hz).

EXAMPLE 37

Compound 38:
Isomer ratio: about 2:1
FAB-MS m/z: 535 [M+H]$^+$
Major component: $^1$H—NMR (CDCl$_3$) δ(ppm): 7.25 (1H, m), 7.14 (1H, s), 6.68 (1H, 16.2 Hz), 6.44 (1H, s), 6.16 (1H, dd, 11.2, 10.9 Hz), 5.72 (1H, dd, 10.1, 2.8 Hz), 5.49 (1H, m), 4.74 (1H, br), 4.64 (1H, 16.5 Hz), 4.57 (1H, 16.5 Hz), 4.01 (1H, br), 3.20 (1H, br), 2.93–2.99 (5H, br), 2.76 (4H, br), 2.45 (1H, m), 2.37 (6H, s), 1.97 (1H, m), 1.56 (3H, d, 6.6 Hz).

EXAMPLE 38

Compound 39:
According to (1-1) described in Example 1, an oxime derivative was prepared from radicicol and trifluoroacetate of compound a, and then compound 39 was prepared according to (1-2) described in Example 1.
Isomer ratio: about 5:1
FAB-MS m/z: 589 [M+H]$^+$
Major component: $^1$H—NMR (CDCl$_3$+CD$_3$OD) δ(ppm): 10.85 (1H, br), 7.90 (1H, br), 7.16 (1H, m), 6.67 (1H, d, 15.8 Hz), 6.58 (1H, s), 6.15 (1H, dd, 11.6, 10.6 Hz), 5.64 (1H, br d, 9.9 Hz), 5.50 (1H, m), 4.75 (1H, br), 4.19 (2H, m), 4.02 (1H, br), 3.55 (2H, br), 3.40 (2H, br), 3.19 (1H, br), 2.97 (1H, ddd, 7.9, 2.4, 2.4 Hz), 2.29–2.36 (3H, m), 1.99 (1H, ddd, 15.2, 8.9, 4.0 Hz), 1.59–1.64 (1H, br), 1.56 (3H, d, 6.6 Hz), 1.37 (6H, br).

EXAMPLE 39

Compound 40:
According to Example 38, compound 40 was prepared from a trifluoroacetate of compound b.
Isomer ratio: about 2:1
FAB-MS m/z: 631 [M+H]$^+$
Major component: $^1$H—NMR (CDCl$_3$) δ(ppm): 11.03 (1H, br), 8.72 (1H, br), 7.16 (1H, dd, 15.8, 12.9 Hz), 6.67 (1H, d, 16.2 Hz), 6.58 (1H, s), 6.14 (1H, dd, 11.2, 9.9 Hz), 5.62 (1H, br d, 9.6 Hz), 5.49 (1H, m), 4.72 (1H, br), 4.05–4.21 (3H, m), 3.56 (2H, br), 3.40 (2H, br), 3.21 (1H, br), 2.97 (1H, ddd, 8.3, 2.3, 2.3 Hz), 2.29–2.37 (3H, m), 2.01 (1H, ddd, 15.2, 8.6, 4.3 Hz), 1.60–1.76 (10H, br), 1.55 (3H, d, 6.6 Hz), 1.28 (12H, br)

EXAMPLE 40

Compound 41
According to (1-2) described in Example 1, 14 mg (yield, 10%) of compound 41 was prepared from 100 mg (0.228 mmol) of compound (K), 52 mg (0.342 mmol) of HOBt, 65 mg (0.342 mmol) of EDCI and 69 mg (0.274 mmol) of pentaethylene glycol monomethyl ether. The thus prepared compound 41 was found to be a mixture of oxime-based isomers (about 3:1) according to $^1$H—NMR.
FAB-MS m/z: 672 [M+H]$^+$
Major component: $^1$H—NMR (CDCl$_3$) δ(ppm): 7.20 (1H, m), 6.77 (1H, d, 16.2 Hz), 6.58 (1H, s), 6.16 (1H, dd, 11.6, 10.6 Hz), 5.66 (1H, br d, 9.6 Hz), 5.53 (1H, m), 4.77 (1H, br), 4.76 (1H, d, 16.5 Hz), 4.69 (1H, 16.2 Hz), 4.33 (2H, m)r, 4.00 (1H, br), 3.72 (2H, m), 3.64–3.65 (14H, m), 3.53–3.56 (2H, m), 3.37 (3H, s), 3.20 (1H, br), 2.98 (1H, br d, 8.6 Hz), 2.34 (1H, ddd, 15.2, 3.6, 3.3 Hz), 2.00 (1H, ddd, 15.5, 8.6, 4.0 Hz), 1.56 (3H, d, 6.6 Hz).

EXAMPLE 41

Compound 42:
According to Example 40, compound 42 was prepared from compound (K).
Isomer ratio: about 3:1
FAB-MS m/z: 584 [M+H]$^+$
Major component: $^1$H—NMR (CDCl$_3$) δ(ppm): 10.80 (1H, br), 7.20 (1H, m), 6.77 (1H, d, 16.2 Hz), 6.58 (1H, br), 6.58 (1H, s), 6.16 (1H, t, 10.9 Hz), 5.67 (1H, br d, 9.9 Hz), 5.51 (1H, m), 4.78 (1H, br), 4.76 (1H, d, 16.5 Hz), 4.69 (1H, d, 16.5 Hz), 4.31–4.35 (2H, m), 4.02 (1H, br), 3.73 (2H, t, 4.8 Hz), 3.63–3.67 (6H, m), 3.54–3.57 (2H, m), 3.38 (3H, s), 3.19 (1H, br), 2.98 (1H, ddd, 9.2, 3.3, 3.3 Hz), 2.34 (1H, ddd, 15.2, 3.6, 3.3 Hz), 1.98 (1H, ddd, 18.8, 8.9, 4.0 Hz), 1.57 (3H, d, 6.9 Hz).

EXAMPLE 42

Compound 43:
According to (1-1) described in Example 1, 338 mg (yield, 53%) of compound 43 was prepared from 500 mg (1.37 mmol) of radicicol and 438 mg (2.74 mmol) of o-benzylhydroxylamine hydrochloride. The thus prepared compound 43 was found to be a mixture of oxime-based isomers (about 2:1) according to $^1$H—NMR.
FAB-MS m/z: 470 [M+H]$^+$
Major component: $^1$H—NMR (CD$_3$OD) δ(ppm): 7.10–7.50 (6H, m), 6.78 (1H, d, 15.8 Hz), 6.42 (1H, s), 6.18 (1H, t, 10.9 Hz), 5.59 (1H, dd, 10.9, 3.3 Hz), 5.30 (1H, m), 5.16 (2H, s), 3.91 (1H, d, 16.3 Hz), 3.81 (1H, d, 16.3 Hz), 3.32 (1H, m), 3.01 (1H, dt, 7.9, 3.3 Hz), 2.41 (1H, dd, 14.3, 3.5 Hz), 1.55 (1H, m), 1.52 (3H, d, 6.4 Hz).

EXAMPLE 43

Compound 44:
A 205 mg (1.12 mmol) portion of compound c was dissolved in 3 ml of methanol, and the solution was mixed with 0.467 ml of 12 N hydrochloric acid and stirred at room temperature for 2.5 hours. The solvent was evaporated under reduced pressure, the thus prepared residue was dissolved in 2 ml of pyridine and mixed with 136 mg (0.37 mmol) of radicicol which had been dissolved in 2 ml of pyridine, and then the mixture was stirred at room temperature for 138 hours. The reaction solution was mixed with 0.5 N hydrochloric acid and extracted with ethyl acetate. The ethyl acetate layer was washed with saturated brine and dried with anhydrous sodium sulfate, and then the solvent was evaporated under reduced pressure. The resulting residue was purified by thin layer chromatography (chloroform/methanol=5/1, then chloroform/acetone=4/1) to obtain 119 mg (yield, 65%) of compound 44. The thus prepared compound 44 was found to be a mixture of oxime-based isomers (about 2.5:1) according to $^1$H—NMR.
FAB-MS m/z: 486 [M+H]$^+$
Major component: $^1$H—NMR (CDCl$_3$) δ(ppm): 11.00 (1H, br), 9.09 (1H, br), 7.22–7.32 (3H, m), 7.00 (1H, d, 8.2 Hz), 6.91 (1H, ddd, 7.6, 7.3, 1.1 Hz), 6.64 (1H, d, 15.8 Hz), 6.57 (1H, s), 6.14 (1H, dd, 9.9, 9.6 Hz), 5.69 (1H, br d, 10.2 Hz), 5.47 (1H, m), 5.15 (1H, d, 13.5 Hz), 5.08 (1H, d, 12.9 Hz), 4.80 (1H, br), 3.99 (1H, br), 3.20 (1H, br), 2.96 (1H, ddd, 8.3, 2.6, 2.5 Hz), 2.31 (1H, ddd, 15.2, 3.6, 3.3 Hz), 1.97 (1H, ddd, 14.9, 8.6, 4.0 Hz), 1.55 (3H, d, 6.6 Hz).

EXAMPLES 44–49

According to Example 43, compounds 45 to 50 were prepared from radicicol and compounds d to i, respectively.

EXAMPLE 44

Compound 45:
Isomer ratio: about 1.7:1
FAB-MS m/z: 502 [M+H]$^+$
Major component: $^1$H—NMR (CDCl$_3$+CD$_3$OD) δ(ppm): 7.11 (1H, dd, 16.2, 11.2 Hz), 6.67 (1H, d, 16.2 Hz), 6.37 (1H, s), 6.35 (1H, d, 2.0 Hz), 6.32 (1H, d, 2.0 Hz), 6.18 (1H, d, 2.0 Hz), 6.05 (1H, t, 10.6 Hz), 5.54 (1H, dd, 10.1, 2.8 Hz), 5.36 (1H, m), 4.97 (2H, s), 4.36 (1H, d, 16.2 Hz), 3.86 (1H, d, 18.1 Hz), 3.16 (1H, br), 2.91 (1H, br d, 8.9 Hz), 2.26 (1H, ddd, 14.9, 3.3, 3.0 Hz), 1.77 (1H, ddd, 14.9, 4.3, 4.0 Hz), 1.47 (3H, d, 6.6 Hz).

EXAMPLE 45

Compound 46:
Isomer ratio: about 1.8:1
FAB-MS m/z: 560 [M+H]$^+$
Major component: $^1$H—NMR (CDCl$_3$) δ(ppm): 7.17 (1H, dd, 15.8, 11.5 Hz), 6.73 (1H, d, 16.2 Hz), 6.63 (2H, s), 6.54 (1H, s), 6.13 (1H, dd, 12.5, 10.6 Hz), 5.60 (1H, br d, 11.2 Hz), 5.49 (1H, m), 5.11 (2H, s), 4.69 (1H, br), 4.04 (1H, br), 3.85 (3H, s), 3.84 (6H, s), 3.18 (1H, br), 2.96 (1H, br d, 8.9 Hz), 2.32 (1H, ddd, 14.9, 3.6, 3.3 Hz), 1.95 (1H, ddd, 14.5, 9.4, 4.1 Hz), 1.54 (39, d, 6.6 Hz).

EXAMPLE 46

Compound 47:
Isomer ratio: about 1.8:1
FAB-MS m/z: 500 [M+H]$^+$
Major component: $^1$H—NMR (CDCl$_3$) δ(ppm): 7.16 (1H, dd, 16.5, 11.2 Hz), 6.74 (1H, d, 16.2 Hz), 6.52 (1H, s), 6.21 (1H, d, 2.0 Hz), 6.18 (1H, d, 2.0 Hz), 6.14 (1H, dd, 10.9, 10.6 Hz), 5.98 (1H, dd, 3.6, 2.0 Hz), 5.65 (1H, br d, 10.2 Hz), 5.49 (1H, m), 5.02 (1H, s), 4.70 (1H, br), 3.99 (1H, br), 3.18 (1H, br), 2.96 (1H, ddd, 8.9, 3.3, 2.6 Hz), 2.32 (1H, ddd, 15.2, 3.6, 3.3 Hz), 1.96 (1H, ddd, 15.0, 9.4, 4.5 Hz), 1.55 (3H, d, 6.9 Hz).

EXAMPLE 47

Compound 48:
Isomer ratio: about 3:1
FAB-MS m/z: 527 [M+H]$^+$
Major component: $^1$H—NMR (CDCl$_3$) δ(ppm): 7.15 (1H, m), 7.14 (2H, d, 8.6 Hz), 6.72 (2H, d, 8.6 Hz), 6.69 (1H, d, 15.8 Hz), 6.56 (1H, s), 6.14 (1H, dd, 11.2, 10.6 Hz), 5.64 (1H, dd, 10.2, 3.3 Hz), 5.50 (1H, m), 4.73 (1H, br), 4.25–4.38 (2H, m), 4.06 (1H, br), 3.21 (1H, br), 2.95–3.00 (3H, m), 2.92 (6H, s), 2.34 (1H, ddd, 15.2, 3.5, 3.32 Hz), 1.99 (1H, ddd, 14.8, 8.9, 4.0 Hz), 1.57 (3H, d, 6.9 Hz).

EXAMPLE 48

Compound 49:
Isomer ratio: about 2.4:1
FAB-MS m/z: 582 [M+H]$^+$
Major component: $^1$H—NMR (CDCl$_3$) δ(ppm): 7.38 (2H, d, 7.9 Hz), 7.14–7.32 (1H, m), 7.23 (2H, d, 7.6 Hz), 6.71 (1H, d, 15.8 Hz), 6.38 (1H, s), 6.15 (1H, dd, 11.9, 10.6 Hz), 5.64 (1H, dd, 10.2, 2.0 Hz), 5.47 (1H, m), 5.17 (2H, s), 4.70 (1H, br), 3.68 (1H, br), 3.66 (2H, s), 3.21 (1H, br), 2.97 (1H, br d, 8.3 Hz), 2.61 (8H, br), 2.37 (3H, s), 2.33 (1H, ddd, 14.2, 3.6, 3.3 Hz), 1.99 (1H, m), 1.54 (3H, d, 6.6 Hz).

EXAMPLE 49

Compound 50:
Isomer ratio: about 1.4:1
FAB-MS m/z: 577 [M+H]$^+$
Major component: $^1$H—NMR (CDCl$_3$) δ(ppm): 7.88 (1H, d, 7.9 Hz), 7.71 (1H, m), 7.57 (1H, dd, 7.9, 7.3 Hz), 7.42 (1H, d, 8.3, 7.3 Hz), 7.19 (1H, m), 6.79 (1H, d, 16.2 Hz), 6.56 (1H, s) 6.17 (1H, dd, 10.9, 9.6 Hz), 5.59–5.72 (3H, m), 5.51 (1H, m), 4.66 (1H, br), 3.96 (1H, br), 3.20 (1H, br), 2.99 (1H, ddd, 8.6, 2.6, 2.6 Hz), 2.80 (6H, s), 2.34 (1H, ddd, 15.2, 3.6, 3.3 Hz), 1.97 (1H, m), 1.56 (3H, d, 6.6 Hz).

EXAMPLE 50

Compound 51:
A 565 mg (4.55 mmol) portion of compound j was dissolved in 10 ml of pyridine, and the solution was mixed with 0.4 ml of concentrated hydrochloric acid and 664 mg (1.82 mmol) of radicicol and stirred at room temperature for 21 hours. The reaction solution was mixed with a saturated ammonium chloride aqueous solution and extracted with ethyl acetate, the ethyl acetate layer was washed with saturated brine and dried with anhydrous sodium sulfate, and then the solvent was evaporated under reduced pressure. The resulting residue was purified by silica gel column chromatography (chloroform/methanol=40/1) to obtain 694 mg (yield, 81%) of compound 51.
Isomer ratio: about 2:1
FAB-MS m/z: 471 [M+H]$^+$
Major component: $^1$H—NMR (CD$_3$OD) δ(ppm): 8.48 (1H, d, 4.0 Hz), 7.84 (1H, dt, 7.6, 1.8 Hz), 7.53 (1H, m), 7.33 (1H, m), 7.26 (1H, dd, 16.2, 11.2 Hz), 6.87 (1H, d, 15.8 Hz), 6.40 (1H, s), 6.17 (1H, t, 10.9 Hz), 5.60 (1H, dd, 10.9, 3.0 Hz), 5.28 (1H, m), 5.23 (2H, s), 3.92 (1H, d, 16.2 Hz), 3.77 (1H, d, 16.2 Hz), 3.33 (1H, m), 3.01 (1H, m), 2.40 (1H, ddd, 14.2, 3.6, 3.3 Hz), 1.58 (1H, ddd, 13.8, 8.9, 4.4 Hz), 1.51 (3H, d, 6.3 Hz).

EXAMPLE 51

Compounds 52 and 53:
A mixture of compounds 52 and 53 (about 4:1) was prepared from radicicol and compound k according to Example 50, 380 mg of the thus prepared mixture of compounds 52 and 53 (about 4:1) was separated by high performance liquid chromatography (column: YMC-Pack ODS AM, SH-365-10AM, 500×30 mm I. D., eluent: 50 mM phosphate buffer (pH 7.3)/methanol=47/53, flow rate: 40 ml/min, detection: UV 276 nm), the eluate was extracted with ethyl acetate, washed with saturated brine and dried with anhydrous sodium sulfate, and then the solvent was evaporated under reduced pressure. Each of the resulting residues was powdered from a mixed solvent of ethanol and water to obtain 219 mg of compound 52 and 133 mg of compound 53.
Compound 52:
FAB-MS m/z: 471 [M+H]$^+$
$^1$H—NMR (CD$_3$OD) δ(ppm): 8.58 (1H, d, 2.0 Hz), 8.47 (1H, dd, 5.0, 2.0 Hz), 7.89 (1H, dd, 7.9, 2.0 Hz), 7.43 (1H, ddd, 7.9, 5.0, 2.0 Hz), 7.26 (1H, dd, 15.8, 10.9 Hz), 6.76 (1H, d, 15.8 Hz), 6.41 (1H, s), 6.16 (1H, t, 10.9 Hz), 5.61 (1H, dd, 10.9, 3.0 Hz), 5.31 (1H, m), 5.22 (2H, s), 3.91 (1H, d, 15.8 Hz), 3.81 (1H, d, 16.3 Hz), 3.35 (1H, m), 3.02 (1H, m), 2.42 (1H, dt, 15.3, 4.0 Hz), 1.58 (1H, ddd, 13.8, 8.9, 4.4 Hz), 1.52 (3H, d, 6.4 Hz).
Compound 53:
FAB-MS m/z: 471 [M+H]$^+$
$^1$H—NMR (CD$_3$OD) δ(ppm): 8.61 (1H, d, 2.0 Hz), 8.49 (1H, dd, 5.0, 2.0 Hz), 7.93 (1H, dd, 7.9, 2.0 Hz), 7.45 (1H, ddd, 7.9, 5.0, 2.0 Hz), 7.15 (1H, dd, 16.2, 10.9 Hz), 6.41 (1H, s), 6.12 (1H, d, 15.8 Hz), 6.09 (1H, t, 10.9 Hz), 5.48 (1H, dd, 10.9, 3.0 Hz), 5.31 (1H, m), 5.26 (2H, s), 4.64 (1H, d, 16.4 Hz), 3.40 (1H, d, 16.2 Hz), 3.35 (1H, m), 2.96 (1H, dt, 8.9, 2.6 Hz), 2.42 (1H, dt, 14.5, 3.0 Hz), 1.60 (1H, m), 1.50 (3H, d, 6.4 Hz).

EXAMPLE 52

Compound 54:

According to Example 50, compound 54 was prepared from radicicol and compound m.

Isomer ratio: about 2:1

FAB-MS m/z: 471 [M+H]+

Major component: $^1$H—NMR (CD$_3$OD) δ(ppm): 8.60 (2H, m), 7.50 (1H, m), 7.29 (1H, dd, 16.2, 11.2 Hz), 6.85 (1H, d, 11.2 Hz), 6.43 (1H, s), 6.18 (1H, t, 10.9 Hz), 5.62 (1H, dd, 10.6, 3.3 Hz), 5.30 (1H, m), 5.23 (2H, s), 3.91 (1H, d, 16.2 Hz), 3.81 (1H, d, 16.2 Hz), 3.35 (1H, m), 3.02 (1H, dt, 7.9, 3.3 Hz), 2.42 (1H, dd, 14.5, 4.0 Hz), 1.59 (1H, ddd, 13.8, 8.9, 4.4 Hz), 1.52 (3H, d, 6.3 Hz).

EXAMPLE 53

Compound 55:

According to Example 43, compound 55 was prepared from radicicol and compound n.

Isomer ratio: about 1.5:1

FAB-MS m/z: 499 [M+H]+

Major component: $^1$H—NMR (CDCl$_3$) δ(ppm): 8.47 (1H, s), 8.42 (1H, d, 5.0 Hz), 7.62 (1H, d, 7.9 Hz), 7.28 (1H, dd, 7.6, 4.9 Hz), 7.17 (1H, dd, 15.5, 11.5 Hz), 6.63 (1H, d, 16.2 Hz), 6.52 (1H, s), 6.15 (1H, dd, 11.6, 11.2 Hz), 5.65 (1H, br d, 9.9 Hz), 5.50 (1H, m), 4.71 (1H, d, 15.5 Hz), 4.20 (2H, t, 6.8 Hz), 4.01 (1H, br), 3.19 (1H, br), 2.97 (1H, br d, 8.6 Hz), 2.77 (2H, t, 7.3 Hz), 2.33 (2H, ddd, 15.2, 3.3, 3.0 Hz), 2.07 (2H, m), 1.94 (1H, ddd, 16.8, 8.3, 4.0 Hz), 1.56 (3H, d, 6.9 Hz).

EXAMPLE 54

Compound 56:

According to Example 43, compound 56 was prepared from radicicol and compound o.

Isomer ratio: about 3:1

FAB-MS m/z: 487 [M+H]+

Major component: $^1$H—NMR (CDCl$_3$) δ(ppm): 10.95 (15, br), 9.36 (1H, br), 8.15 (1H, d, 4.3 Hz), 7.34 (1H, d, 8.3 Hz), 7.20–7.30 (2H, m), 6.69 (1H, d, 16.2 Hz), 6.57 (1H, s), 6.15 (1H, dd, 10.9, 10.6 Hz), 5.70 (1H, br d, 11.2 Hz), 5.48 (1H, m), 5.32 (1H, d, 12.5 Hz), 5.24 (1H, d, 12.5 Hz), 4.77 (1H, br), 4.03 (1, br), 3.19 (1H, br), 2.96 (1H, br d, 8.2 Hz), 2.32 (1H, ddd, 15.2, 3.3, 3.0 Hz), 1.97 (1H, ddd, 14.7, 8.7, 4.3 Hz), 1.55 (3H, d, 6.6 Hz).

EXAMPLE 55

Compound 57:

(55-1):

A 5.00 g (13.7 mmol) portion of radicicol was dissolved in 10 ml of DMF to which, while cooling in an ice bath, were subsequently added 2.80 g (41.1 mmol) of imidazole and 4.54 g (30.1 mmol) of tert-butyl(chloro)dimethylsilane, and the resulting mixture was stirred at room temperature for 3 hours. The reaction solution was mixed with a saturated ammonium chloride aqueous solution and extracted with ethyl acetate, the ethyl acetate layer was washed with saturated brine and dried with anhydrous sodium sulfate, and then the solvent was evaporated under reduced pressure. The resulting residue was purified by silica gel column chromatography (chloroform/methanol=100/1) to obtain 6.96 g (yield, 86%) of a di-tert-butyldimethylsilyl derivative of radicicol.

FAB-MS m/z: 593 [M+H]+

(55-2):

According to (1-1) described in Example 1, 18 mg (yield, 5.5%) of compound (L) was prepared from 319 mg (0.54 mmol) of di-tert-butyldimethylsilyl derivative of radicicol and 240 mg (3.45 mmol) of hydroxylamine hydrochloride. The thus prepared compound (L) was found to be a mixture of oxime-based isomers (about 1:1) according to $^1$H—NMR.

FAB-MS m/z: 608 [M+N]+

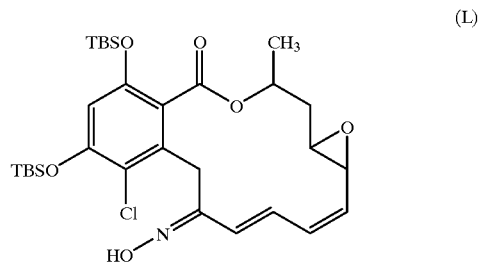

(L)

(55-3):

A 120 mg (0.20 mmol) portion of compound (L) was dissolved in 1.7 ml of THF, the resulting solution was mixed with 167 mg (0.99 mmol) of 2-hydroxymethyl-3-methoxymethoxypyridine dissolved in 0.5 ml of THF, which had been prepared by dimethoxymethylation of 3-hydroxy-2-pyridinecarboxylic acid and subsequent reduction with lithium aluminum hydride, 103 mg (0.39 mmol) of triphenylphosphine and 0.06 ml (0.39 mmol) of DEAD, and the mixture was stirred at room temperature for 23 hours. The reaction solution was mixed with a phosphate buffer (pH 7) and extracted with ethyl acetate. The ethyl acetate layer was washed with saturated brine and dried with anhydrous sodium sulfate, and then the solvent was evaporated under reduced pressure. The resulting residue was purified by thin layer chromatography (chloroform/methanol=100/1) to obtain 39 mg (yield, 26%) of a di-tert-butyldimethylsilyl derivative of compound 57.

FAB-MS m/z: 761 [M+H]+

(55-4):

A 39 mg (0.05 mmol) portion of the di-tert-butyldimethylsilyl derivative of compound 57 was dissolved in 1.8 ml of THF, 0.13 ml (0.13 mmol) of a 1 M TBAF/THF solution was added to the thus prepared solution which was cooled at −10° C., and the resulting mixture was stirred for 50 minutes at the same temperature. The reaction solution was mixed with a phosphate buffer (pH 7) and extracted with chloroform. The chloroform layer was washed with saturated brine and dried with anhydrous sodium sulfate, and then the solvent was evaporated under reduced pressure. The resulting residue was purified by thin layer chromatography (chloroform/methanol =12/1) to obtain 26 mg (yield, 95%) of compound 57. The thus prepared compound 57 was found to be a mixture of oxime-based isomers (about 1:1.7) according to $^1$H—NMR.

FAB-MS m/z: 531 [M+H]+

Major component: $^1$H—NMR (CDCl$_3$) δ(ppm): 11.15 (1H, br), 8.28 (1H, dd, 4.6, 1.3 Hz), 7.49 (1H, d, 8.3 Hz), 7.25 (1H, dd, 8.3, 5.0 Hz), 7.02 (1H, dd, 16.2, 10.9 Hz), 6.72 (1H, s), 6.13 (1H, d, 15.8 Hz), 6.09 (1H, dd, 10.2, 9.6 Hz), 5.55 (1H, dd, 10.6, 2.3 Hz), 5.49 (1H, m), 5.30 (2H, s), 5.23 (2H, s), 4.58 (1H, d, 16.5 Hz), 4.21 (1H, d, 16.5 Hz), 3.45 (3H, s), 3.08 (1H, br), 2.90 (1H, br d, 9.9 Hz), 2.31 (1H, ddd, 15.2, 3.0, 2.6 Hz), 1.90 (1H, ddd, 15.2, 10.2, 4.3 Hz), 1.53 (3H, d, 6.9 Hz).

EXAMPLE 56

Compound 58:
According to Example 43, compound 58 was prepared from radicicol and compound p.
Isomer ratio: about 1.4:1
FAB-MS m/z: 487 [M+H]$^+$
Major component: $^1$H—NMR (CDCl$_3$+CD$_3$OD) δ(ppm): 8.15 (0.25H, dd, 5.9, 3.3 Hz), 7.76 (0.25H, dd, 5.9, 3.3 Hz), 7.64 (1H, m), 7.33 (1H, dd, 3.3, 2.6 Hz), 7.11 (1H, dd, 16.0, 11.4 Hz), 6.56 (1H, d, 16.2 Hz), 6.50 (0.5H, d, 1.7 Hz), 6.38 (1H, s), 6.05 (1H, dd, 10.9, 9.6 Hz), 5.56 (1H, dd, 10.2, 3.0 Hz), 5.37 (1H, m), 4.86 (2H, s), 4.46 (1H, d, 16.5 Hz), 3.88 (1H, d, 16.5 Hz), 3.18 (1H, br), 2.90 (1H, ddd, 8.6, 2.6, 2.3 Hz), 2.27 (1H, ddd, 14.9, 4.3, 3.6 Hz), 1.79 (1H, ddd, 14.5, 8.9, 4.0 Hz), 1.47 (3H, d, 6.3 Hz).

EXAMPLE 57

Compound 59:
According to (1-1) described in Example 1, compound 59 was prepared from radicicol and a trifluoroacetate of compound q.
Isomer ratio: about 2:1
FAB-MS m/z: 504 [M+H]$^+$
Major component: $^1$H—NMR (CD$_3$OD) δ(ppm): 7.29 (1H, dd, 15.8, 11.2 Hz), 6.82 (1H, d, 16.2 Hz), 6.43 (1H, s), 6.18 (1H, dd, 9 Hz), 5.67 (1H, s), 5.66 (1H, dd, 10.6, 3.6 Hz), 5.31 4.87 (2H, s), 3.95 (1H, d, 16.2 Hz), 3.84 (1H, d, 3.30 (1H, m), 3.02 (1H, dd, 5.6, 2.3 Hz), 2.43 (1H, 3.5 Hz), 1.62 (1H, m), 1.52 (3H, d, 6.6 Hz).

EXAMPLE 58

60:
According to Example 43, compound 60 was prepared radicicol and compound r.
ratio: about 2:1
FAB-MS m/z: 491 [M+H]$^+$
Component: $^1$H—NMR (CDCl$_3$) δ(ppm): 8.88 (2H, br), 7.19 6.66 (1H, d, 12.9 Hz), 6.38 (1H, s), 6.16 (1H, dd, Hz), 5.62 (1H, br d, 10.2 Hz), 5.42 (1H, m), 4.59 (1H, 4.00 (3H, m), 3.11–3.31 (3H, m), 2.95 (1H, br d, 53 (3H, s), 2.11–2.33 (3H, m), 1.95 (1H, m), 1.78 1.53 (3H, d, 6.6 Hz).

EXAMPLE 59

61:
According to (1-1) described in Example 1, compound prepared from radicicol and a hydrochloride of s.
ratio: about 1.8:1
FAB-MS m/z: 477 [M+H]$^+$
Major component: $^1$H—NMR (CD$_3$OD) δ(ppm): 7.27 (1H, dd, 16.5, 11.6 Hz), 6.75 (1H, d, 16.5 Hz), 6.39 (1H, s), 6.15 (1H, dd, 11.6, 10.6 Hz), 5.61 (1H, dd, 10.6, 3.6 Hz), 5.32 (1H, m), 4.38 (2H, m), 3.95 (2H, m), 3.28 (1H, m), 3.20 (2H, m), 3.03 (4H, m), 2.95 (1H, m), 2.41 (1H, m), 1.95 (4H, m), 1.66 (1H, m), 1.52 (3H, d, 6.3 Hz).

EXAMPLE 60

Compound 62:
According to (1-1) described in Example 1, compound 62 was prepared from radicicol and a hydrochloride of compound t.
Isomer ratio: about 5:1
FAB-MS m/z: 505 [M+H]$^+$
Major component: 1H—NMR (CD$_3$OD) δ(ppm): 7.26 (1H, dd, 15.8, 10.9 Hz), 6.72 (1H, d, 16.2 Hz), 6.42 (1H, s), 6.16 (1H, dd, 11.9, 10.6 Hz), 5.62 (1H, dd, 10.6, 3.6 Hz), 5.30 (1H, m), 4.23 (2H, dd, 12.5, 6.3 Hz), 3.96 (1H, d, 16.2 Hz), 3.81 (1H, d, 16.2 Hz), 3.35 (1H, m), 3.15 (6H, m), 3.03 (1H, m), 2.44 (1H, dt, 14.5, 3.6 Hz), 2.15 (2H, m), 1.80–1.86 (4H, m), 1.66 (1H, m), 1.52 (3H, d, 6.3 Hz).

EXAMPLE 61

Compound 63:
According to (1-1) described in Example 1, compound 63 was prepared from radicicol and a hydrochloride of compound u.
Isomer ratio: about 2:1
FAB-MS m/z: 521 [M+H]$^+$
Major component: $^1$H—NMR (CD$_3$OD) δ(ppm): 7.25 (1H, dd, 16.2, 11.9 Hz), 6.72 (1H, d, 16.2 Hz), 6.44 (1H, s), 6.16 (1H, dd, 11.9, 10.6 Hz), 5.61 (1H, dd, 10.6, 3.6 Hz), 5.31 (1H, m), 4.24 (2H, m), 3.96 (1H, d, 16.2 Hz), 3.89 (1H, m), 3.83 (1H, d, 16.2 Hz), 3.43 (1H, m), 3.35 (1H, m), 2.96–3.10 (5H, m), 2.43 (1H, dt, 10.9, 3.6 Hz), 1.95–2.20 (4H, m), 1.75–1.80 (4H, m), 1.62 (1H, m), 1.52 (3H, d, 6.6 Hz).

EXAMPLE 62

Compound 64:
According to (1-1) described in Example 1, compound 64 was prepared from radicicol and a hydrochloride of compound v.
Isomer ratio: about 3:1
FAB-MS m/z: 521 [M+H]$^+$
Major component: $^1$H—NMR (CD$_3$OD) δ(ppm): 7.24 (1H, dd, 16.2, 11.9 Hz), 6.73 (1H, d, 16.2 Hz), 6.42 (1H, s), 6.15 (1H, m), 5.60 (1H, dd, 10.8, 4.0 Hz), 5.30 (1H, m), 4.17 (2H, m), 3.92 (1H, d, 16.2 Hz), 3.80 (1H, d, 16.2 Hz), 3.70 (2H, m), 3.35 (1H, m), 3.27 (4H, m), 3.02 (1H, ddd, 8.9, 3.3, 2.0 Hz), 2.41–2.56 (7H, m), 1.70 (5H, m), 1.53 (3H, d, 6.6 Hz).

EXAMPLE 63

Compound 65:
According to (1-1) in Example 1, compound 65 was prepared from radicicol and a hydrochloride of compound w.
Isomer ratio: about 4:1
FAB-MS m/z: 520 [M+H]$^+$
Major component: $^1$H—NMR (CD$_3$OD) δ(ppm): 7.24 (1H, dd, 16.2, 11.2 Hz), 6.71 (1H, d, 16.2 Hz), 6.42 (1H, s), 6.15 (1H, dd, 10.9, 9.6 Hz), 5.60 (1H, dd, 10.9, 3.3 Hz), 5.31 (1H, m), 4.18 (2H, dt, 4.3, 2.0 Hz), 3.93 (1H, d, 15.8 Hz), 3.83 (1H, d, 15.8 Hz), 3.35 (1H, m), 3.02 (1H, dd, 8.9, 2.3 Hz), 2.45–2.60 (1H, m), 2.45 (1H, dt, 14.5, 3.6 Hz), 2.36 (3H, s), 1.92 (2H, m), 1.62 (1H, m), 1.53 (3H, d, 6.6 Hz).

EXAMPLE 64

Compound 66:
According to (1-1) described in Example 1, compound 66 was prepared from radicicol and a hydrochloride of compound x.
Isomer ratio: about 1.5:1
FAB-MS m/z: 596 [M+H]$^+$
Major component: $^1$H—NMR (CD$_3$OD) δ(ppm): 7.20–7.30 (3H, m), 6.95 (2H, d, 7.9 Hz), 6.84 (1H, t, 7.4 Hz), 6.74 (1H, d, 16.2 Hz), 6.43 (1H, s), 6.11 (1H, m), 5.59 (1H, dd, 10.6, 3.3 Hz), 5.30 (1H, m) 4.20 (2H, m), 3.95 (1H, d, 15.8 Hz), 3.84 (1H, d, 15.8 Hz), 3.34 (1H, m), 3.19 (4H, m), 3.01 (1H, dd, 5.6, 3.3 Hz), 2.71 (4H, m), 2.52 (2H, m), 2.40 (1H, dd, 14.5, 3.6 Hz), 1.74 (4H, m), 1.61 (1H, m), 1.51 (3H, d, 6.6 Hz)

EXAMPLE 65

Compound 67:
According to (1-1) described in Example 1, compound 67 was prepared from radicicol and a hydrochloride of compound y.
Isomer ratio: about 2:1
FAB-MS m/z: 537 [M+H]$^+$
Major component: $^1$H—NMR (CD$_3$OD) δ(ppm): 7.24 (1H, dd, 16.2, 11.2 Hz), 6.73 (1H, d, 16.2 Hz), 6.42 (1H, s), 6.15

(1H, dd, 10.9, 9.6 Hz), 5.59 (1H, dd, 10.9, 3.3 Hz), 5.30 (1H, m), 4.11–4.19 (2H, m), 3.94 (1H, d, 16.2 Hz), 3.84 (1H, d, 16.2 Hz), 3.34 (1H, m), 3.00 (1H, m), 2.78 (4H, m), 2.67 (4H, m), 2.47 (3H, m), 1.67 (5H, m), 1.53 (3H, d, 6.6 Hz).

EXAMPLE 66

Compounds 68 and 69:

According to (1-1) described in Example 1, a mixture of compounds 68 and 69 was prepared from radicicol and a hydrochloride of compound z, and then compounds 68 and 69 were prepared by purifying the mixture using high performance liquid chromatography (eluent: 50 mM phosphate buffer (pH 5.9)/acetonitrile=68/32) according to Example 51.

Compound 68: FAB-MS m/z: 491 [M+H]$^+$
$^1$H—NMR (CDCl$_3$) δ(ppm): 10.08 (1H, br s), 7.18 (1H, dd, 15.5, 11.5 Hz), 6.85 (1H, br s), 6.63 (1H, d, 15.5 Hz), 6.60 (1H, s), 6.15 (1H, t, 11.5 Hz), 5.67 (1H, d, 11.5 Hz), 5.51 (1B, m), 4.73 (1H, br), 4.29 (2H, t, 5.3 Hz), 4.03 (1H, br), 3.64 (2H, m), 3.51 (3H, m), 3.20 (1H, s), 2.98 (1H, m), 2.40 (2H, m), 2.33 (1H, m), 2.01 (2H, m), 1.57 (3H, d, 6.9 Hz).

Compound 69: FAB-MS m/z: 491 [M+H]$^+$
$^1$H—NMR (CDCl$_3$) δ(ppm): 11.25 (1H, br s), 7.02 (1H, dd, 16.0, 11.2 Hz), 6.58 (1H, br s), 6.11 (1H, d, 16.0 Hz), 6.09 (1H, m), 5.57 (1H, d, 10.9 Hz), 5.51 (1H, m), 4.45 (1H, d, 16.5 Hz), 4.34 (2H, d, 5.2 Hz), 4.25 (1H, d, 16.5 Hz), 3.80 (1H, m), 3.58 (3H, m), 3.08 (1H, s), 2.91 (1H, d, 9.9 Hz), 2.45 (2H, m), 2.32 (1H, m), 2.06 (2H, m), 1.95 (1H, m), 1.56 (3H, d, 6.9 Hz).

EXAMPLE 67

Compound 70:

According to Example 50, compound 70 was prepared from radicicol and compound aa.
Isomer ratio: about 2:1
FAB-MS m/z: 505 [M+H]$^+$
Major component: $^1$H—NMR (CD$_3$OD) δ(ppm): 7.25 (1H, dd, 16.2, 11.8 Hz), 6.75 (1H, d, 16.2 Hz), 6.43 (1H, s), 6.17 (1H, t, 11.2 Hz), 5.60 (1H, dd, 10.6, 3.6 Hz), 5.30 (1H, m), 4.18 (2H, m), 3.92 (1H, d, 16.2 Hz), 3.79 (1H, d, 16.2 Hz), 3.49 (2H, m), 3.41 (2H, q, 6.9 Hz), 3.34 (1H, m), 3.02 (1H, m), 2.43 (1H, m), 2.37 (2H, m), 2.04 (2H, m), 1.98 (2H, m), 1.62 (1H, m), 1.53 (3H, d, 6.6 Hz).

EXAMPLE 68

Compound 71:

According to (1-1) described in Example 1, compound 71 was prepared from radicicol and a trifluoroacetate of compound bb.
Isomer ratio: about 3:1
FAB-MS m/z: 507 [M+H]$^+$
Major component: $^1$H—NMR (CD$_3$OD) δ(ppm): 7.24 (1H, dd, 16.5, 11.2 Hz), 6.77 (1H, d, 16.2 Hz), 6.45 (1H, s), 6.17 (1H, dd, 10.9, 9.6 Hz), 5.61 (1H, m), 5.29 (1H, m), 4.11–4.90 (3H, m), 3.99 (1H, d, 16.2 Hz), 3.81 (1H, d, 16.2 Hz), 3.39 (4H, m), 3.31 (1H, m), 3.01 (1H, m), 2.43 (1H, dt, 14.5, 3.6 Hz), 2.07 (4H, m), 1.60 (1H, m), 1.51 (3H, d, 6.6 Hz).

EXAMPLE 69

Compound 72:

According to Example 50, compound 72 was prepared from radicicol and compound cc.
Isomer ratio: about 2:1
FAB-MS m/z: 580 [M+H]$^+$
Major component: $^1$H—NMR (CD$_3$OD) δ(ppm): 7.24 (1H, dd, 16.2, 11.2 Hz), 6.72 (1H, d, 16.2 Hz), 6.43 (1H, s), 6.11 (1H, dd, 11.9, 10.6 Hz), 5.59 (1H, dd, 10.6, 3.3 Hz), 5.31 (1H, m), 4.99 (1H, t, 5.0 Hz), 3.81–3.99 (6H, m), 3.35 (1H, m), 2.99 (1H, m), 2.42 (1H, dt, 14.5, 3.5 Hz), 2.03 (2H, m), 1.61 (1H, ddd, 14.2, 4.6, 4.6 Hz), 1.53 (3H, d, 6.3 Hz).

EXAMPLE 70

Compound 73:
(70-1):

A 300 mg (0.493 mmol) portion of compound (L) was dissolved in 5 ml of dichloromethane to which were subsequently added 0.05 ml (0.493 mmol) of ethyl chloroformate and 0.07 ml (0.493 mmol) of triethylamine at −78° C., and the mixture was stirred at 0° C. for 2 hours. The reaction solution was mixed with a saturated ammonium chloride aqueous solution and extracted with ethyl acetate. The ethyl acetate layer was washed with saturated brine and dried with anhydrous sodium sulfate, and then the solvent was evaporated under reduced pressure. The resulting residue was purified by silica gel column chromatography (n-hexane/ethyl acetate=6/1) to obtain 188 mg (yield, 56%) of a di-tert-butyldimethylsilyl derivative of compound 73.

(70-2):

According to (55-4) described in Example 55, compound 73 was prepared from the di-tert-butyldimethylsilyl derivative of compound 73.
Isomer ratio: about 1.3:1
Major component: $^1$H—NMR (CD$_3$OD) δ(ppm): 7.45 (1H, dd, 16.3, 11.4 Hz), 6.71 (1H, d, 15.8 Hz), 6.46 (1H, s), 6.22 (1H, m), 5.73 (1H, dd, 10.4, 3.0 Hz), 5.33 (1H, m), 4.34 (1H, d, 6.9 Hz), 4.11 (1H, d, 16.3 Hz), 4.00 (1H, d, 16.3 Hz), 3.35 (1H, m), 3.04 (1H, m), 2.43 (1H, dt, 14.3, 3.5 Hz), 1.61 (1H, m), 1.53 (3H, d, 6.4 Hz), 1.35 (3H, t, 6.9 Hz).

EXAMPLE 71

Compound 74:

According to (70-1) and (70-2) described in Example 70, compound 74 was prepared from compound (L), triethylamine and methyl isocyanate.
Isomer ratio: about 1.2:1
Major component: $^1$H—NMR (CD$_3$OD) δ(ppm): 7.42 (1H, dd, 16.3, 11.9 Hz), 6.76 (1H, d, 16.3 Hz), 6.46 (1H, s), 6.26 (1H, dd, 11.9, 10.6 Hz), 5.71 (1H, dd, 10.9, 3.5 Hz), 5.34 (1H, m), 4.10 (1H, d, 16.3 Hz), 3.85 (1H, d, 16.3 Hz), 3.36 (1H, m), 3.04 (1H, m), 2.85 (3H, s), 2.43 (1H, dt, 14.3, 3.5 Hz), 1.65 (1H, m), 1.53 (3H, d, 6.4 Hz).

EXAMPLE 72

Compound 75:

According to (70-1) and (70-2) described in Example 70, compound 75 was prepared from compound (L), triethylamine and acetyl chloride.
Isomer ratio: about 1.2:1
Major component: H—NMR (CD$_3$OD) δ(ppm): 7.43 (1H, dd, 15.8, 11.9 Hz), 6.75 (1H, d, 15.8 Hz), 6.47 (1H, s), 6.15 (1H, dd, 11.9, 10.6 Hz), 5.72 (1H, dd, 10.4, 3.5 Hz), 5.34 (1H, m), 4.13 (1H, d, 16.3 Hz), 4.04 (1H, d, 16.3 Hz), 3.35 (1H, m), 3.04 (1H, m), 2.40 (1H, dt, 14.3, 3.5 Hz), 2.23 (3H, s), 1.65 (1H, m), 1.53 (3H, d, 6.9 Hz).

EXAMPLE 73

Compound 76:

According to (1-1) described in Example 1, compound 76 was prepared from radicicol and O-phenylhydroxylamine hydrochloride.
Isomer ratio: about 3:1
FAB-MS m/z: 456 [M+H]$^+$
Major component: $^1$H—NMR (CDCl$_3$) δ(ppm): 10.95 (1H, br), 7.24–7.38 (5H, m), 7.05 (1H, m)), 6.89 (1H, d, 16.2 Hz), 6.61 (1H, s), 6.23 (1H, ddd, 10.2, 10.2, 1.1 Hz), 5.73 (1H, br d, 10.2 Hz), 5.53 (1H, m), 4.85 (1H, br), 4.21 (1H, br), 3.23 (1H, br), 3.01 (1H, ddd, 8.3, 2.6, 2.3 Hz), 2.37 (1H, ddd, 15.2, 3.6, 3.3 Hz), 2.01 (1H, ddd, 15.5, 9.1, 3.8 Hz), 1.58 (3H, d, 6.6 Hz).

REFERENCE EXAMPLE 1

Compound a:

(1-1):

A 5.00 g (22.4 mmol) portion of 8-bromooctanoic acid was dissolved in a mixed solvent of 2 ml dichloromethane and 10 ml hexane, and the solution was mixed with 8.00 ml (44.8 mmol) of tert-butyl 2,2,2-trichloroacetoimidate and 0.45 ml (3.66 mmol) of boron trifluoride-ether complex and stirred at room temperature for 1 hour. The reaction solution was mixed with 10 ml of hexane and 0.031 g (3.66 mmol) of sodium bicarbonate, the resulting precipitate was separated by filtration, and then the solvent was evaporated under reduced pressure. The resulting residue was purified by silica gel column chromatography (n-hexane/ethyl acetate=5/1) to obtain 2.34 g (yield, 38%) of tert-butyl 8-bromooctanoate.

(1-2):

A 2.70 g (8.29 mmol) portion of tert-butyl 8-bromooctanoate was dissolved in 20 ml of DMF, and the solution was mixed with 1.35 g (8.28 mmol) N-hydroxyphthalimide and 1.86 ml (12.4 mmol) of 1,8-diazabicyclo[5,4,0]-7-undecene and stirred at room temperature for 20.5 hours. The reaction solution was mixed with water and extracted with ethyl acetate, the ethyl acetate layer was washed with 0.5 N hydrochloric acid and then with saturated brine and dried with anhydrous sodium sulfate, subsequently evaporating the solvent under reduced pressure. The resulting residue was purified by silica gel column chromatography (n-hexane/ethyl acetate=5/1) to obtain 0.83 g (yield, 28%) of tert-butyl 8-(phthalimidoxy)-octanoate.

$^1$H—NMR (CDCl$_3$) δ(ppm): 7.83 (2H, m), 7.75 (2H, m), 4.20 (2H, t, 6.8 Hz), 2.21 (2H, t, 7.6 Hz), 1.79 (2H, m), 1.60 (2H, m), 1.44 (9H, s), 1.45–1.29 (6H, m).

(1-3):

A 1.00 g (2.77 mmol) portion of tert-butyl 8-(phthalimidoxy)-octanoate was dissolved in 9 ml of chloroform, and the solution was mixed with 4.1 ml (4.16 mmol) of a 1 M hydrazine monohydrate/methanol solution and stirred at room temperature for 0.5 hour. After separation of the resulting precipitate by filtration, the resulting filtrate was mixed with water and extracted with chloroform, the chloroform layer was washed with saturated brine and dried with anhydrous sodium sulfate, and then the solvent was evaporated under reduced pressure. The thus prepared residue was dissolved in 14 ml of dichloromethane, and the solution was mixed with 6.4 ml of trifluoroacetic acid and stirred at room temperature for 2 hours. By evaporating the solvent under reduced pressure, a trifluoroacetate of the compound a was prepared.

REFERENCE EXAMPLE 2

Compound b:

According to (1-1) to (1-3) described in Reference Example 1, a trifluoroacetate of compound b was prepared from 11-bromoundecanoic acid.

REFERENCE EXAMPLE 3

Compound c:

(3-1):

According to (1-2) described in Reference Example 1, 1.29 g (quantitative) of methyl 2-methoxymethoxybenzoate was prepared from 1.00 g (6.57 mmol) of methyl salicylate, 0.75 ml (9.86 mmol) of chloromethyl methyl ether and 1.72 ml (9.86 mmol) of diisopropylethylamine.

(3-2):

A 792 mg (4.04 mmol) portion of methyl 2-methoxymethoxybenzoate dissolved in 12 ml of THF was added to 337 mg (8.89 mmol) of lithium aluminum hydride dissolved in 5 ml of THF, and the mixture was stirred at room temperature for 2.5 hours. The reaction solution was mixed with water and extracted with ethyl acetate, and the ethyl acetate layer was washed with saturated brine and dried with anhydrous sodium sulfate. By evaporation of the solvent under reduced pressure, 640 mg (yield, 94%) of 2-methoxymethoxybenzyl alcohol was prepared.

(3-3):

According to (55-3) described in Example 55, 486 mg (yield, 57%) of N-(2-methoxymethoxybenzyloxy) phthalimide was prepared from 454 mg (2.70 mmol) of 2-methoxymethoxybenzyl alcohol, 484 mg (2.97 mmol) of N-hydroxyphthalimide, 744 mg (2.84 mmol) of triphenylphosphine and 0.446 ml (2.84 mmol) of DEAD.

(3-4):

According to (1-3) described in Reference Example 1, a reaction solution prepared by treating 427 mg (1.36 mmol) of N-(2-methoxymethoxybenzyloxy)phthalimide with 0.099 ml (2.04 mmol) of hydrazine monohydrate was separated by filtration, and then the solvent was evaporated under reduced pressure to obtain 244 mg (yield, 98%) of compound c.

FAB-MS m/z: 184 [M+H]$^+$ $^1$H—NMR (CDCl$_3$) δ(ppm): 7.37 (1H, dd, 7.4, 1.8 Hz), 7.27 (1H, ddd, 7.4, 7.3, 1.8 Hz), 7.11 (1H, dd, 7.3, 1.3 Hz), 7.02 (1H, ddd, 7.6, 7.6, 1.3 Hz), 5.42 (2H, br s), 5.22 (2H, s), 4.79 (2H, s), 3.49 (3H, s).

REFERENCE EXAMPLE 4

Compound d:

According to (55-1) described in Example 55, methyl 3,5-di-(tert-butyldimethylsiloxy)benzoate was prepared from methyl 3,5-dihydroxybenzoate, and compound d was prepared from methyl 3, 5-di-(tert-butyldimethylsiloxy) benzoate according to (3-2) to (3-4) described in Reference Example 3.

FAB-MS m/z: 384 [M+H]$^+$ $^1$H—NMR (CDCl$_3$) δ(ppm): 6.46 (2H, d, 2.3 Hz), 6.28 (1H, t, 2.3 Hz), 5.37 (2H, br), 4.57 (2H, s), 0.97 (18H, s), 0.19 (12H,

REFERENCE EXAMPLE 5

Compound e:

According to (3-2) to (3-4) described in Reference Example 3, compound e was prepared from methyl 3,4,5-trimethoxybenzoate.

FAB-MS m/z: 214 [M+H]$^+$ $^1$H—NMR (CDCl$_3$) δ(ppm): 6.60 (2H, s), 5.43 (2H, br), 4.64 (2H, s), 3.88 (6H, s), 3.85 (3H, s).

REFERENCE EXAMPLE 6

Compound f:

(6-1):

A 2.00 g (13.1 mmol) portion of 3,5-diaminobenzoic acid was dissolved in a mixed solvent of 20 ml THF and 20 ml water, and the solution was mixed with 6.88 g (31.5 mmol) of di-tert-butyl dicarbonate, adjusted to pH 7 to 8 with a saturated sodium bicarbonate aqueous solution and then stirred at room temperature for 4 hours. The reaction solution was mixed with a 10% citric acid aqueous solution and extracted with ethyl acetate. The ethyl acetate layer was washed with saturated brine and dried with anhydrous sodium sulfate, and then the solvent was evaporated under reduced pressure. The resulting residue was purified by silica gel column chromatography (chloroform/methanol=10/1) to obtain 3.93 g (yield, 85%) of 3,5-di-(tert-butoxycarbonylamino)benzoic acid.

(6-2):

A 2.00 g (5.68 mmol) portion of 3,5-di-(tert-butoxycarbonylamino)benzoic acid was dissolved in 15 ml of THF, 3.77 ml (39.7 mmol) of borane-methyl sulfide complex dissolved in 10 ml of THF was added dropwise to the thus prepared solution, and the mixture was stirred at room temperature for 5 hours. The reaction solution was cooled to 0° C., mixed with water and extracted with ethyl acetate. The ethyl acetate layer was washed with saturated brine and dried with anhydrous sodium sulfate, and then the solvent was evaporated under reduced pressure. The resulting residue was purified by silica gel column chromatography (chloroform/methanol=20/1) to obtain 1.08 g (yield, 56%) of 1,3-di-tert-butoxycarbonylamino-5-hydroxymethylbenzene.

(6-3):

According to (3-3) and (3-4) described in Reference Example 3, compound f was prepared from 1,3-di-tert-butoxycarbonylamino-5-hydroxymethylbenzene.

FAB-MS m/z: 354 [M+H]$^+$ $^1$H—NMR (CDCl$_3$) δ(ppm): 7.41 (1H, t, 1.7 Hz), 7.07 (2H, d, 1.7 Hz), 6.50 (2H, br s), 5.39 (2H, br), 4.62 (2H, s), 1.50 (18H, s).

REFERENCE EXAMPLE 7

Compound g:

According to (3-3) and (3-4) described in Reference Example 3, compound g was prepared from 4-(dimethylamino)phenetyl alcohol.

FAB-MS m/z: 181 [M+H]$^+$ $^1$H—NMR (CDCl$_3$) δ(ppm): 7.10 (2H, d, 8.6 Hz), 6.70 (2H, d, 8.6 Hz), 5.38 (2H, br s), 3.84 (2H, t, 7.1 Hz), 2.91 (6H, s), 2.81 (2H, t, 7.1 Hz).

REFERENCE EXAMPLE 8

Compound h:

According to (6-2) and (6-3) described in Reference Example 6, compound h was prepared from 4-(N-methylpiperazinomethyl)benzoic acid.

$^1$H—NMR (CDCl$_3$) δ(ppm): 7.29 (2H, m), 7.15 (2H, m), 5.20 (2H, br), 4.56 (2H, s), 3.93 (2H, s), 3.44–3.41 (4H, br), 2.68–2.58 (4H, m), 2.55 (3H, s).

REFERENCE EXAMPLE 9

Compound i:

According to (1-2) described in Reference Example 1, methyl 2-(dimethylaminosulfonyl)benzoate was prepared from methyl 2-(aminosulfonyl)benzoate, methyl iodide and potassium carbonate, and then compound i was prepared according to (3-2) to (3-4) described in Reference Example 3.

FAB-MS m/z: 231 [M+H]$^+$

1H—NMR (CDCl$_3$+CD$_3$OD) δ(ppm): 7.87 (1H, d, 7.9 Hz), 7.71 (1H, d, 7.6 Hz), 7.62 (1H, dd, 7.9, 7.3 Hz), 7.46 (1H, dd, 7.6, 7.3 Hz), 5.10 (2H, s), 2.81 (6H, s).

REFERENCE EXAMPLE 10

Compound j:

According to (3-3) and (3-4) described in Reference Example 3, compound j was prepared from 2-pyridylcarbinol.

$^1$H—NMR (CDCl$_3$) δ(ppm): 7.21–7.30 (5H, m), 5.40 (2H, br) 3.90 (2H, t, 6.9 Hz), 2.91 (2H, t, 6.9 Hz).

REFERENCE EXAMPLE 11

Compound k:

According to (3-3) and (3-4) described in Reference Example 3, compound k was prepared from 3-pyridylcarbinol.

$^1$H—NMR (CDCl$_3$) δ(ppm): 8.63 (1H, d, 2.0 Hz), 8.57 (1 H, dd, 5.0, 1.5 Hz), 7.73 (1H, dt, 7.9, 2.0 Hz), 7.33 (1H, dd, 7.9, 4.9 Hz), 4.92 (2H, br), 4.71 (2H, s).

REFERENCE EXAMPLE 12

Compound m:

According to (3-3) and (3-4) described in Reference Example 3, compound m was prepared from 4-pyridylcarbinol.

$^1$H—NMR (CDCl$_3$) δ(ppm): 8.59 (2H, d, 5.9 Hz), 7.26 (2H, d, 5.9 Hz), 5.55 (2H, br), 4.71 (2H, s).

REFERENCE EXAMPLE 13

Compound n:

According to (3-3) and (3-4) described in Reference Example 3, compound n was prepared from 3-pyridinepropanol.

$^1$H—NMR (CDCl$_3$) δ(ppm): 8.45 (1H, br s), 8.43 (1H, dd, 4.9, 1.3 Hz), 7.50 (1H, ddd, 7.6, 1.6, 1.3 Hz), 7.20 (1H, dd, 7.6, 4.9 Hz), 5.36 (2H, br), 3.67 (2H, t, 6.3 Hz), 2.67 (2H, t, 7.8 Hz), 1.90 (2H, m).

REFERENCE EXAMPLE 14

Compound o:

According to (3-1) to (3-4) described in Reference Example 3, compound o was prepared from 3-hydroxypicolinic acid.

FAB-MS m/z: 185 [M+H]$^+$ $^1$H—NMR (CDCl$_3$) δ(ppm): 8.27 (1H, dd, 4.6, 1.3 Hz), 7.42 (1H, dd, 8.3, 1.3 Hz), 7.18 (1H, dd, 8.3, 4.6 Hz), 5.75 (2H, br), 5.22 (2H, d, 0.7 Hz), 4.92 (2H, s), 3.47 (3H, d, 1.0 Hz).

REFERENCE EXAMPLE 15

Compound p:

According to (3-1) to (3-4) described in Reference Example 3, compound p was prepared from 6-hydroxynicotinic acid.

$^1$H—NMR (CDCl$_3$+CD$_3$OD) δ(ppm): 7.98 (1H, d, 2.3 Hz), 7.52 (1H, dd, 8.6, 2.3 Hz), 6.68 (1H, d, 8.2 Hz), 5.32 (2H, s), 4.46 (2H, s), 3.35 (3H, s).

REFERENCE EXAMPLE 16

Compound q:

(16-1):

According to (1-2) described in Reference Example 1, tert-butyl N-(6-uracilmethoxy) carbamate was prepared from tert-butyl N-hydroxycarbamate, sodium hydride, and 6-(chloromethyl)uracil.

FAB-MS m/z: 258 [M+H]$^+$ $^1$H—NMR (CDCl$_3$) δ(ppm): 10.34 (1H, br), 8.02 (1H, br), 5.54 (1H, s), 4.67 (2H, s), 1.48 (9H, s).

(16-2):

A 385 mg (1.50 mmol) portion of tert-butyl N-(6-uracilmethoxy) carbamate was dissolved in 0.5 ml of dichloromethane, and the solution was mixed with 0.5 ml of trifluoroacetic acid and stirred at room temperature for 1 hour. By evaporating the solvent under reduced pressure, a trifluoroacetate of compound q was prepared.

REFERENCE EXAMPLE 17

Compound r:

According to (3-3) and (3-4) described in Reference Example 3, compound r was prepared from 1-methyl-3-piperidinemethanol.

$^1$H—NMR (CDCl$_3$) δ(ppm): 5.47 (2H, br), 3.55 (1H, dd, 9.9, 5.6 Hz), 3.48 (1H, dd, 9.9, 7.6 Hz), 2.92 (1H, br d, 10.9 Hz), 2.81 (1H, br d, 11.2 Hz), 2.28 (3H, s), 2.03 (1H, m), 1.89–1.97 (2H, m), 1.59–1.71 (4H, m).

REFERENCE EXAMPLE 18

Compound s:

According to (3-3) described in Reference Example 3, 1-(2-phthalimidoxyethyl) pyrrolidine was prepared from pyrrolidineethanol and treated with a 4 N hydrochloric acid/ethyl acetate solution to make it into a hydrochloride, and then compound s was prepared from the hydrochloride according to (3-4) described in Reference Example 3. By treating compound s with a 4 N hydrochloric acid/ethyl acetate solution, a hydrochloride of compound s was prepared.
FAB-MS m/z: 145 [M+H]$^+$

REFERENCE EXAMPLE 19

Compound t:
(19-1)

According to (1-2) described in Reference Example 1, 4.20 g (yield, 39%) of ethyl N-(3-bromopropoxy) acetoimidate was prepared from 5.00 g (48.5 mmol) of ethyl acetohydroxamate, 1.90 g (48.5 mmol) of sodium hydride and 7.4 ml (72.7 mmol) of 1,3-dibromopropane.
(19-2):

A 500 mg (2.23 mmol) portion of ethyl N-(3-bromopropoxy)acetoimidate was dissolved in 6 ml of dichloromethane, and the solution was mixed with 0.22 ml (2.23 mmol) of piperidine and 0.33 ml (2.23 mmol) of 1,8-diazabicyclo[5.4,0]-7-undecene and stirred at room temperature for 36 hours. The reaction solution was mixed with a saturated ammonium chloride aqueous solution and extracted with chloroform. The chloroform layer was washed with saturated brine and dried with anhydrous sodium sulfate, and then the solvent was evaporated under reduced pressure. The resulting residue was purified by silica gel chromatography (chloroform/methanol=10/1) to obtain 166 mg (yield, 32%) of ethyl N-(3-piperidinopropoxy)acetoimidate.
FAB-MS m/z: 229 [M+H]$^+$
$^1$H—NMR (CDCl$_3$) δ(ppm): 4.00 (2H, q, 6.9 Hz), 3.93 (2H, t, 6.3 Hz), 2.53 (6H, m), 1.93 (2H, m), 1.92 (3H, s), 1.70 (4H, m), 1.49 (2H, m), 1.27 (3H, t, 6.9 Hz).
(19-3):

A 166 mg (0.71 mmol) portion of ethyl N-(3-piperidinopropoxy)acetoimidate was dissolved in 0.5 ml of THF, and the solution was mixed with 0.1 ml of concentrated hydrochloric acid and stirred at room temperature for 1 hour. By evaporating the solvent under reduced pressure, a hydrochloride of compound t was prepared.

REFERENCE EXAMPLE 20

Compound u:

According to (19-2) and (19-3) described in Reference Example 19, a hydrochloride of compound u was prepared from ethyl N-(3-bromopropoxy)acetoimidate.

REFERENCE EXAMPLE 21

Compound v:

According to (19-1) described in Reference Example 19, ethyl N-(4-bromobutoxy)acetoimidate was prepared from ethyl acetohydroxamate, sodium hydride and 1,4-dibromobutane, and then a hydrochloride of compound v was prepared according to (19-2) and (19-3) described in Reference Example 19.

REFERENCE EXAMPLE 22

Compound w:

According to (19-2) and (19-3) described in Reference Example 19, a hydrochloride of compound w was prepared from ethyl N-(3-bromopropoxy)acetoimidate.

REFERENCE EXAMPLE 23

Compound x:

According to (19-2) and (19-3) described in Reference Example 19, a hydrochloride of compound x was prepared from ethyl N-(4-bromobutoxy)acetoimidate.

REFERENCE EXAMPLE 24

Compound y:

According to (19-2) and (19-3) described in Reference Example 19, a hydrochloride of compound y was prepared from ethyl N-(4-bromobutoxy) acetoimidate.

REFERENCE EXAMPLE 25

Compound z:

According to (3-3) and (3-4) described in Reference Example 3, compound z was prepared from 1-(2-hydroxyethyl)-2-pyrrolidinone, and then compound z was treated with a 4 N hydrochloric acid/ethyl acetate solution to obtain a hydrochloride of compound z.
FAB-MS m/z: 145 [M+H]$^+$

REFERENCE EXAMPLE 26

Compound aa:

According to (3-3) and (3-4) described in Reference Example 3, compound aa was prepared from 1-(3-hydroxypropyl)-2-pyrrolidinone.
$^1$H—NMR (CDCl$_3$) δ(ppm): 5.40 (2H, br), 3.68 (2H, t, 6.3 Hz), 3.39 (2H, dd, 11.5, 6.9 Hz), 3.37 (2H, m), 2.39 (2H, dd, 8.6, 7.6 Hz), 2.02 (2H, ddd, 6.9, 6.3, 1.0 Hz), 1.81 (2H, ddd, 11.5, 6.3, 1.0 Hz), 1.81 (2H, m).

REFERENCE EXAMPLE 27

Compound bb:
(27-1):

According to (16-1) described in Reference Example 16, 659 mg (3.80 mmol) of tert-butyl N-(allyloxy)carbamate prepared from tert-butyl N-hydroxycarbamate, sodium hydride and allyl bromide was dissolved in 10 ml of dichloromethane, and the thus prepared solution was mixed with 886 mg (4.67 mmol) of m-chloroperbenzoic acid and stirred at room temperature for 24 hours. The reaction solution was filtered, mixed with a 1 N sodium hydroxide aqueous solution and extracted with chloroform. The chloroform layer was washed with saturated brine and dried with anhydrous sodium sulfate, and then the solvent was evaporated under reduced pressure. The resulting residue was purified by silica gel column chromatography (n-hexane/ethyl acetate=4/1) to obtain 447 mg (yield, 62%) of tert-butyl N-(2,3-epoxypropoxy)carbamate.
(27-2):

A 150 mg (0.79 mmol) portion of tert-butyl N-(2,3-epoxypropoxy)carbamate was dissolved in 1 ml of methanol, and the solution was mixed with 0.08 ml (0.95 mmol) of pyrrolidine and stirred at room temperature for 14 hours. The reaction solution was mixed with a saturated ammonium chloride aqueous solution and extracted with chloroform. The chloroform layer was washed with saturated brine and dried with anhydrous sodium sulfate, and then the solvent was evaporated under reduced pressure to obtain 181 mg (yield, 88%) of tert-butyl N-(2-hydroxy-3-pyrrolidinylpropoxy)-carbamate.
FAB-MS m/z: 261 [M+H]$^+$
$^1$H—NMR (CDCl$_3$) δ(ppm): 4.02 (1H, m), 3.92 (1H, dd, 11.2, 3.3 Hz), 3.77 (1H, dd, 11.2, 7.3 Hz), 2.68 (4H, m), 2.65 (1H, m), 2.50 (1H, m), 1.89 (9H, s), 1.80 (4H, m).

(27-3):

According to (16-2) described in Reference Example 16, a trifluoroacetate of compound bb was prepared from tert-butyl N-(2-hydroxy-3-pyrrolidinylpropoxy) carbamate.

REFERENCE EXAMPLE 28

Compound cc:

According to (1-2) described in Reference Example 1, 2-(2-phthalimidoxyethyl)-1,3-dioxolan was prepared from 2-(2-bromoethyl)-1,3-dioxolan, N-hydroxyphthalimide and potassium carbonate, and then compound cc was prepared from 2-(2-phthalimidoxyethyl)-1,3-dioxolan according to (3-4) described in Reference Example 3.

$^1$H—NMR (CDCl$_3$) δ(ppm): 5.40 (2H, br), 4.97 (1H, t, 5.0 Hz), 3.80–4.00 (6H, m), 1.98 (2H, dt, 6.3, 5.0 Hz).

TABLE 6

H$_2$NO—R$^{3e}$

| Compound | R$^{3e}$ |
|---|---|
| (1) Reference Example | |
| a | (CH$_2$)$_7$CO$_2$H |
| b | (CH$_2$)$_{10}$CO$_2$H |
| c | 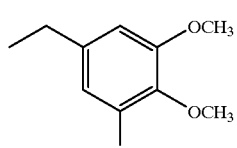 |
| d | 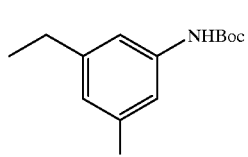 |
| e | 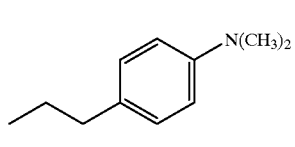 |
| f | 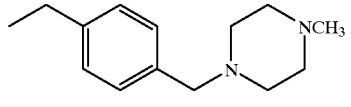 |
| g | 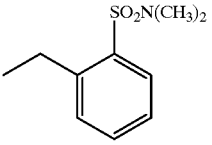 |
| h | 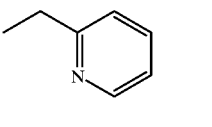 |

TABLE 6-continued

H$_2$NO—R$^{3e}$

| Compound | R$^{3e}$ |
|---|---|
| i | 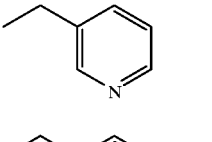 |
| j | 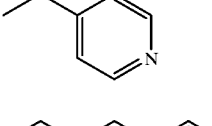 |
| k | 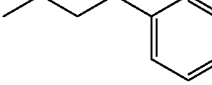 |
| m | 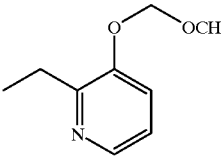 |
| n | 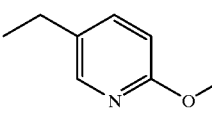 |
| o | 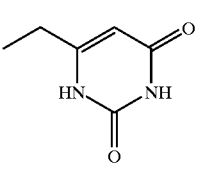 |
| p | 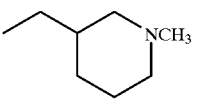 |
| q | 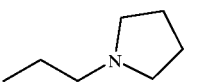 |
| r | 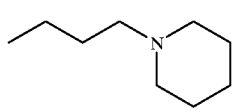 |
| s | 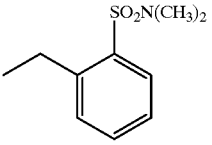 |
| (2) Reference Example | |
| t | 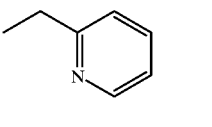 |

TABLE 6-continued

H₂NO—R³ᵉ

| Compound | R³ᵉ |
|---|---|
| u | ![structure](piperidine with butyl, OH) |
| v | ![structure](morpholine with pentyl) |
| w | ![structure](N-methylpiperazine with butyl) |
| x | ![structure](N-phenylpiperazine with pentyl) |
| y | ![structure](thiomorpholine with butyl) |
| z | ![structure](2-pyrrolidinone with propyl) |
| aa | ![structure](2-pyrrolidinone with butyl) |
| bb | ![structure](pyrrolidine with 2-hydroxypropyl) |
| cc | ![structure](1,3-dioxolane with propyl) |

INDUSTRIAL APPLICABILITY

According to the present invention, novel radicicol derivatives or pharmacologically acceptable salts thereof which show tyrosine kinase inhibition activity and have antitumor or immunosuppression effects are provided.

What is claimed is:

1. A radicicol derivative represented by formula (I):

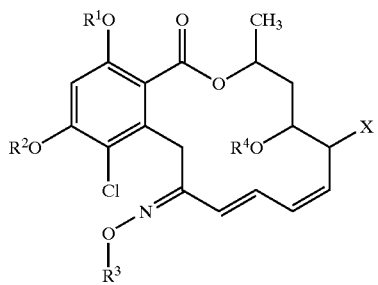

(I)

wherein
$R^1$ and $R^2$ independently represent hydrogen, alkanoyl, alkenoyl, tert-butyldiphenylsilyl or tert-butyldimethylsilyl;

$R^3$ represents Y—$R^5$, wherein Y represents substituted or unsubstituted alkylene and $R^5$ represents substituted or unsubstituted pyridyl, or substituted or unsubstituted pyridonyl, or $R^3$ represents $COR^{13}$, wherein $R^{13}$ represents hydrogen, substituted or unsubstituted lower alkyl, substituted or unsubstituted higher alkyl, substituted or unsubstituted aryl, substituted or unsubstituted lower alkoxy, or $NR^{14}R^{15}$ wherein $R^{14}$ and $R^{15}$ independently represent hydrogen, substituted or unsubstituted lower alkyl, substituted or unsubstituted higher alkyl, substituted or unsubstituted aryl, or substituted or unsubstituted pyridyl, or $R^{14}$ and $R^{15}$ are combined together with adjoining N to represent a substituted or unsubstituted pyridyl group;

X represents halogen, or is combined together with $R^4$ to represent a single bond; and $R^4$ is combined together with X to represent a single bond, or represents hydrogen, alkanoyl, alkenoyl, or —SO—Z, wherein Z is represented by formula (II):

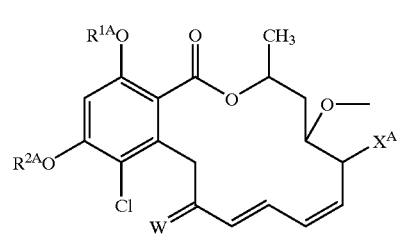

(II)

wherein $R^{1A}$ and $R^{2A}$ have the same meaning as $R^1$ and $R^2$, respectively; $X^A$ represents halogen; and W represents O or N—O—$R^{3A}$ wherein $R^{3A}$ has the same meaning as $R^3$, or a pharmacologically acceptable salt thereof.

2. The compound according to claim 1 wherein X is halogen, or a pharmacologically acceptable salt thereof.

3. The compound according to claim 1 wherein X is combined together with $R^4$ to represent a single bond, or a pharmacologically acceptable salt thereof.

4. The compound according to claim 3 wherein $R^1$ and $R^2$ each is hydrogen, or a pharmacologically acceptable salt thereof.

5. The compound according to claim 4 wherein $R^3$ is Y—$R^5$, or a pharmacologically acceptable salt thereof.

6. The compound according to claim 4 wherein $R^5$ is substituted or unsubstituted pyridyl, or a pharmacologically acceptable salt thereof.

7. A composition, comprising at least one of the compounds or pharmacologically acceptable salts thereof according to any one of claims 1 to 6 together with a pharmacologically acceptable carrier.

8. A method of treating disease mediated by tyrosine kinase, comprising administering to a patient in a need thereof an effective amount of the composition according to claim 7.

9. The compound according to claim 4 wherein $R^5$ is substituted or unsubstituted pyridonyl, or a pharmacologically acceptable salt thereof.

* * * * *